(12) United States Patent
Liang et al.

(10) Patent No.: US 7,348,315 B2
(45) Date of Patent: Mar. 25, 2008

(54) METHODS OF TREATING HEART FAILURE WITH MODIFIED ATP, ADP AND AMP COMPOUNDS

(75) Inventors: Bruce T Liang, Marion Station, PA (US); Kenneth A Jacobson, Silver Spring, MD (US)

(73) Assignee: The University of Connecticut, Farmington, CT (US)

( * ) Notice: Subject to any disclaimer, the term of this patent is extended or adjusted under 35 U.S.C. 154(b) by 691 days.

(21) Appl. No.: 10/396,200

(22) Filed: Mar. 25, 2003

(65) Prior Publication Data

US 2003/0186929 A1 Oct. 2, 2003

Related U.S. Application Data

(63) Continuation of application No. 09/641,491, filed on Aug. 18, 2000, now abandoned, which is a continuation-in-part of application No. 08/875,050, filed as application No. PCT/US96/03911 on Mar. 22, 1996, now Pat. No. 6,255,292, which is a continuation-in-part of application No. 08/409,350, filed on Mar. 23, 1995, now Pat. No. 5,712,258.

(51) Int. Cl.
*A61K 31/70* (2006.01)
*C07H 19/20* (2006.01)

(52) U.S. Cl. ..................... 514/47; 536/26.26

(58) Field of Classification Search .................. 514/47, 514/261; 536/26.21, 26.23, 26.26; 544/264
See application file for complete search history.

(56) References Cited

U.S. PATENT DOCUMENTS

| | | | |
|---|---|---|---|
| 4,657,898 A | 4/1987 | Bristol et al. | 514/47 |
| 4,843,066 A | 6/1989 | Yamada et al. | 514/45 |
| 4,902,677 A | 2/1990 | Imai et al. | 514/47 |
| 4,990,498 A | 2/1991 | Suhadolnik | 514/47 |
| 5,017,564 A | 5/1991 | Makino et al. | 514/47 |
| 5,055,304 A | 10/1991 | Makino et al. | 424/465 |
| 5,104,859 A | 4/1992 | Sollevi | 514/46 |
| 5,140,015 A | 8/1992 | Olsson et al. | 514/46 |
| 5,219,841 A | 6/1993 | Inaba et al. | 514/47 |
| 5,246,922 A | 9/1993 | Kataoka et al. | 514/47 |
| 5,415,873 A | 5/1995 | Trepel et al. | 424/422 |
| 5,430,027 A | 7/1995 | Knutsen et al. | 514/46 |
| 5,516,762 A | 5/1996 | Bertics et al. | 514/47 |
| 5,571,524 A | 11/1996 | Kitakaze et al. | 424/423 |
| 5,712,258 A | 1/1998 | Liang | 514/47 |
| 6,153,647 A | 11/2000 | Mallet et al. | 514/546 |
| 6,255,292 B1 | 7/2001 | Liang et al. | 514/47 |

FOREIGN PATENT DOCUMENTS

| | | |
|---|---|---|
| FR | 1975 M | 8/1963 |
| FR | 7857 M | 4/1970 |
| GB | 853232 | 9/1957 |

OTHER PUBLICATIONS

Barry, W.H., et al., "Mechanisms of transmembrane calcium movement in cultured chick embryo ventricular cells," *J. Physiol.*, 1982, 325, 243-260.

(Continued)

*Primary Examiner*—L. E. Crane
(74) *Attorney, Agent, or Firm*—Cantor Colburn LLP

(57) ABSTRACT

Disclosed herein are methods of using an adenosine analog or derivative for treating heart failure, increasing cardiac muscle contractility, increasing cardiac diastolic relaxation, and increasing vasodilation. Exemplary adenosine analogs/derivatives include compounds of the following formula

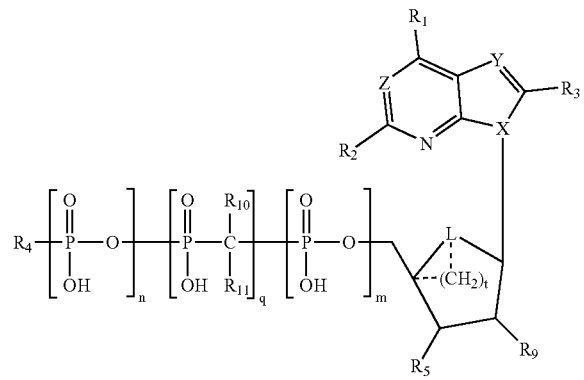

wherein
L is CH or O, wherein when L is CH, t is 1 and when L is O, t is 0;
$R_1$ is halogen or $—R_6—(R_7)_p—R_8$;
$R_2$ is hydrogen, alkyl, cycloalkyl, cycloalkenyl, alkynyl, alkylthio, aminoalkylthio, halogen, or $—R_6—(R_7)_p—R_8$;
$R_3$ is H, halogen or $—R_6—(R_7)_p—R_8$;
$R_4$ is —OH or —SH;
$R_5$ is —OH or $—R_6—(R_7)_p—R_8$;
$R_6$ is NH or S;
$R_7$ is $CH_2$;
$R_8$ is H, $NH_2$, halogen, CN, CCH, cycloallkyl, having 3 to about 10 carbon atoms or aryl having 3 to about 20 carbon atoms;
$R_9$ is OH or acetamido;
$R_{10}$ and $R_{11}$ are independently hydrogen or halogen;
X, Y, and Z are independently N or CH;
m is 0, 1, or 2;
n is 0 or 1;
q is 0 or 1 if L is CH, or if L is O, $R_3$ is halogen or $—R_6—(R_7)_p—R_8$;
q is 1 if L is O, $R_3$ is H, halogen, or $—R_6—(R_7)_p—R_8$;
provided that at least one of m, n, and q is 1; and
p is 0 to 10.

46 Claims, 15 Drawing Sheets

OTHER PUBLICATIONS

Burnstock, G., et al., "Structure activity relationships for derivatives of adenosine-5'-triphosphate as agonists at $P^2$ purinoceptors: heterogeneity within $P^{2x}$ and $P^{2y}$ subtypes," *Drug Development Res.*, 1994, 31, 206-219.

Fischer, et al., "Identification of potent, selective $P_{2y}$- purinoceptor agonists: structure-activity relationships for 2-thioether derivatives of adenosine 5'-triphosphate," *J. Med. Chem.*, 1993, 36, 3937-3946.

Fukunaga, et al., "Hypotensive effects of adenosine and adenosine triphosphate compared with sodium nitroprusside," *Anesth. Analg.*, 1982, 61(3), 273-278.

Gui, J., et al., "A serine kinase regulates intracellular localization of splicing factors in the cell cycle," *Nature*, 1994, 369, 678-682.

Hoffman, B., et al., "Diogitalis and allied cardiac glycosides," in The Pharmacological Basis of Therapeutics, Gliman, A.G., et al. (Eds.), *Pergamon Press*, 1990, Chapter 34, 814-839.

Kelly, R.A., et al., "Endothelin enhances the contractile responsiveness of adult rat ventricular myocytes to calcium by a pertussis toxin-sensitive pathway," *J. Clin. Invest.*, 1990, 86, 1164-1171.

Kennedy, "P1 and P2-purinoceptor subtypes—an update," *Arch. Intl. Pharmacodynamie et de Therapie*, 1990, 303, 30-50.

Kikugawa, K., et al., "Platelet aggregation inhibitors. IX. Chemical transformation of adenosine into 2-thioadenosine derivatives," *Chemical Pharm. Bull.*, 1977, 25, 1959-1969.

Kovacs, t., et al., "Simple synthesis of 5-vinyl-and 5-ethynyl-2'deoxyuridine-5'-triphosphates," *Tetrahedron Letts.*, 1988, 29(36), 4525-4528.

MacFarlane, et al., "2-methylthioadenosine[beta-$^{32}$P]diphosphate—an agonist and radioligand for the receptor that inhibits the accumulation of cyclic AMP in intact blood platlets," *J. Chem. Invest.*, 1983, 71, 420-425.

Munson, P., et al., "LIGAND: a versatile computerized approach for characterization of ligand-binding systems," *Analytical Biochem.*, 1980, 107, 220-239.

Murray, et al., "Adenosine 5'-phosphorothioate. A nucleotide analog that is a subtrate, competitive inhibitor, or regulator of some enzymes that interact with adenosine 5'-phosphate," *Biochem.*, 1968, 7(11), 4023-4029.

Nielsen, et al., "Sodium imidodiphosphatel. Synthesis, identification and hydrolytic degradation," *Synthesis and Identification of Sodium Imidodiphosphate*, 1961, 83, 99-102.

Novgorodov, S., et al., "Expression of porcine leukocyte 12-lipoxygenase in a baculovirus-insect cell system and its characterization," *Arch. Biochem. Biophys.*, 1994, 312, 219-226.

Podrasky, E., et al., "Positive inotropic effect mediated by a novel stimulatory $P^{2y}$-like purinergic receptor in cultured fetal ventricular myocyte," *FASEB J.*, 1994, 8(5), 3686.

Rotrosen, D., et al., "Production of recombinant cytochrome b558 allows reconstitution of the phagocyte NADPH oxidase solely from recombinant proteins," *J. Biol. Chem.*, 1993, 268, 14256-14260.

Sen, L., et al., "Enhanced $\alpha$1-adrenergic responsiveness in cardiomypoathic hamster cardiac myocytes: relation to the expression of pertussis toxin-sensitive G protein and $\alpha$1-adrenergic receptors," *Circ. Res.*, 1990, 67, 1182-1192.

Watson, S., et al., "The G-protein linked receptor factsbook," *Academic Press*, NY, 1994, 30-31.

Williams, "Purine receptors in mammalian tissues: pharmacology and functional significance," *Ann. Rev. Pharm. Toxicol.*, 1987, 27, 316-318.

Xu, H., et al., "High-efficiency gene transfer into cardiac myocytes," *Nucl. Acids Res.*, 1992, 20(23), 6425-6426.

Xu, D., et al., "Expression and pharmacological characterization of a stimulatory subtype of adenosine receptor in ventricular myocyte," *Circ. Res.*, 1992, 70, 56-65.

Yount, et al., "Adenyl imidodiphosphate, an adenosine triphosphate analog containing a P-N-P linkage," *Biochem.*, 1971, 10(13), 2484-2489.

Zheng, J-S., et al., "Extracellular adenosine-triphosphate (ATP_inhibits cardiac myocyte hypertrophy induced by adrenergic angonists," *Circulation*, 1994, 90(4), 1039.

Marumoto, et al., "A new method for synthesis of nucleoside 3', 5'-cyclic phosphates. Cyclization of nucleoside 5'-trichloromethylphosphonates," *Chem. & Pharm. Bulletin*, Oct. 1975, 23(10), 2295-2300.

Sigma Chemical Company, Biochemicals—Organic Compounds for Research and Diagnostic Reagents (Catalog), St. Louis, MO, 1992, 45-46, 48, 53-54 and 663.

Abiru, et al., *J. Med. Chem.*, 2000, 35, 2253-2260.

Jacobsen, et al., "Methanocarba analogues of purine nucleosides as potent and selective adenosine receptor agonists," *J. Med. Chem.*, 2000, 23, 2196-2203.

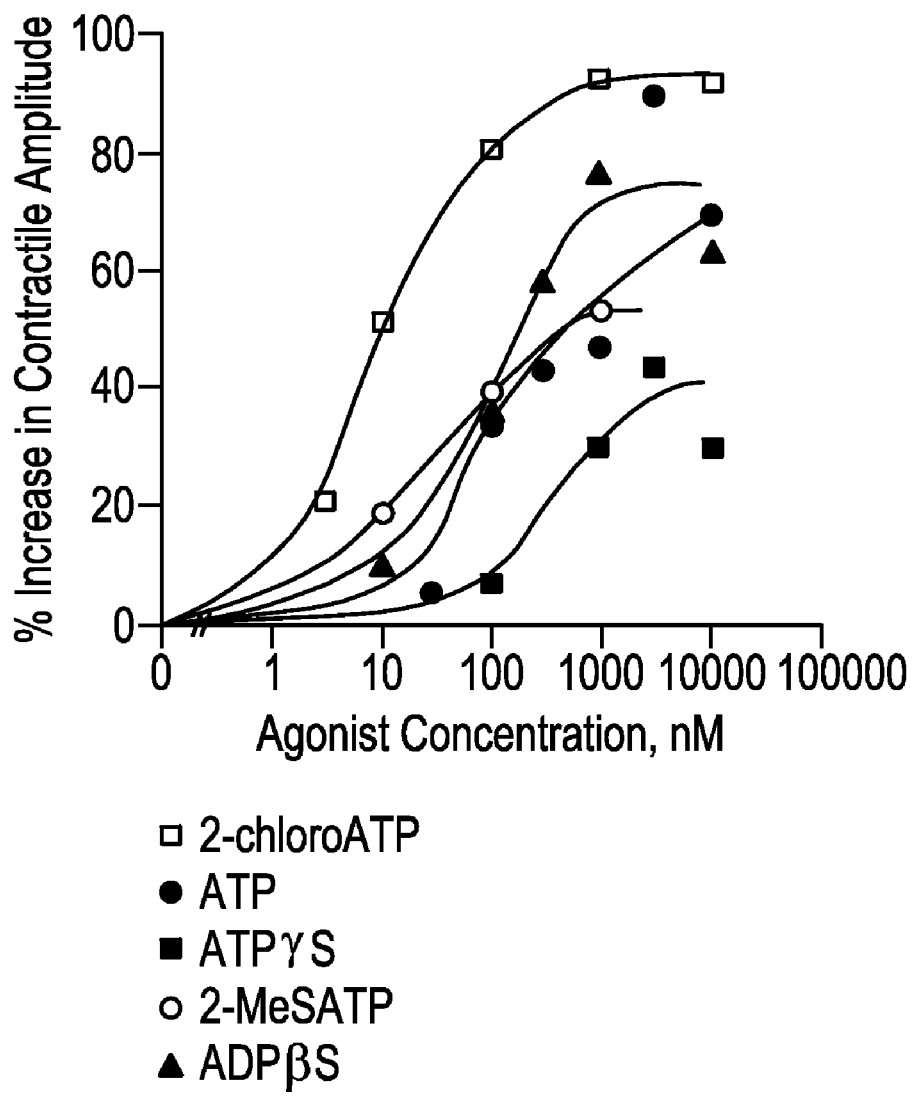

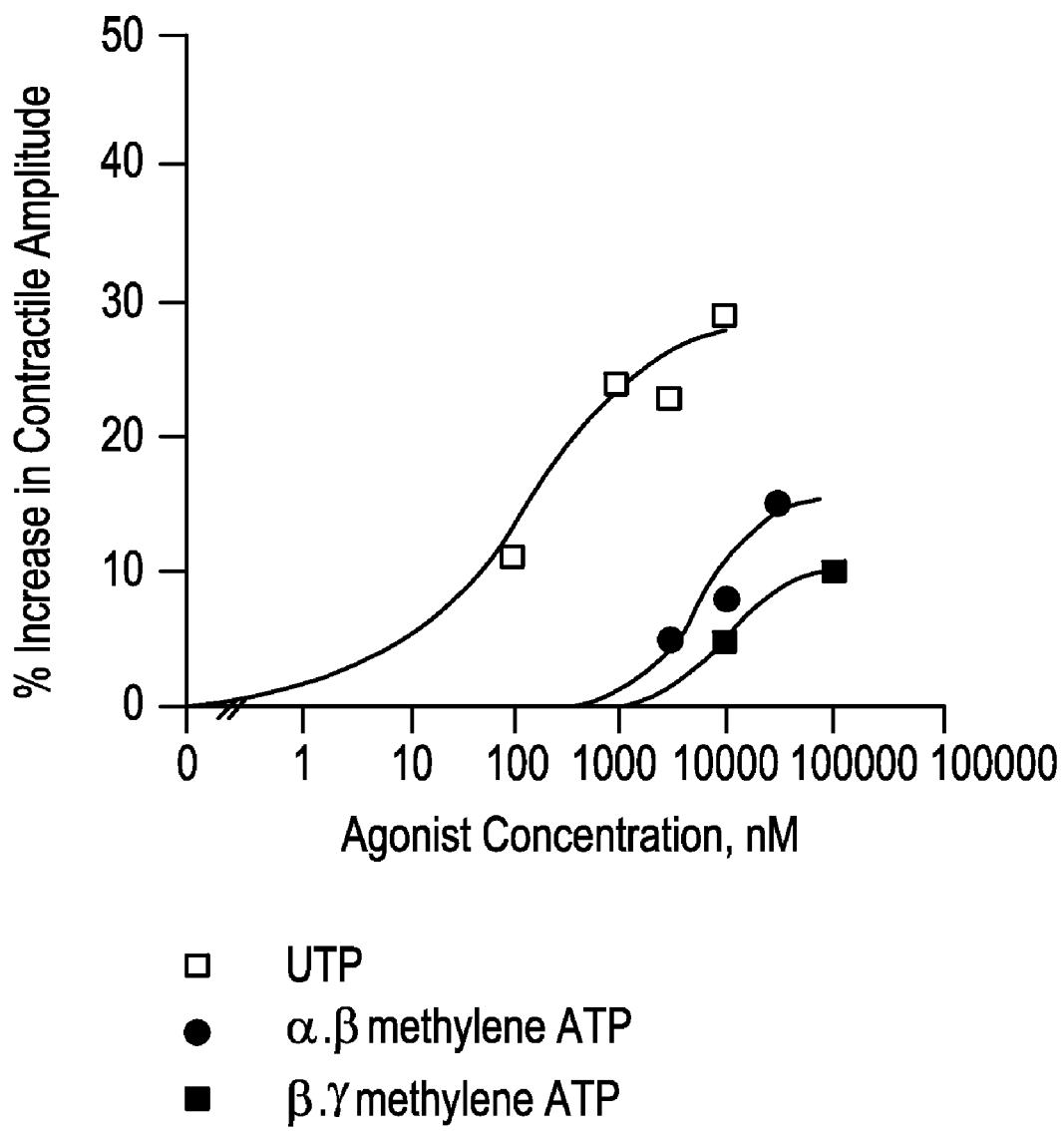

FIG. 10

Table 1: Effects of P2 Receptor and Beta-adrenergic Receptor Agonists on the Cardiac Function of Work-performing Mouse Heart.

| Parameters | Basal | 2-meSATP | Basal* | ISO |
|---|---|---|---|---|
| +dP/dt | 2738 ± 97 | 3258 ± 97 | 3002 ± 52 | 5694 ± 292 |
| -dP/dt | 2343 ± 95 | 2666 ± 97 | 2636 ± 79 | 3386 ± 257 |
| C.O. | 5 ± 0.11 | 5.5 ± 0.17 | 7 ± 0.5 | 8.6 ± 0.5 |
| H.R. | 422 ± 10.7 | 423 ± 15 | 447 ± 17 | 617 ± 31 |

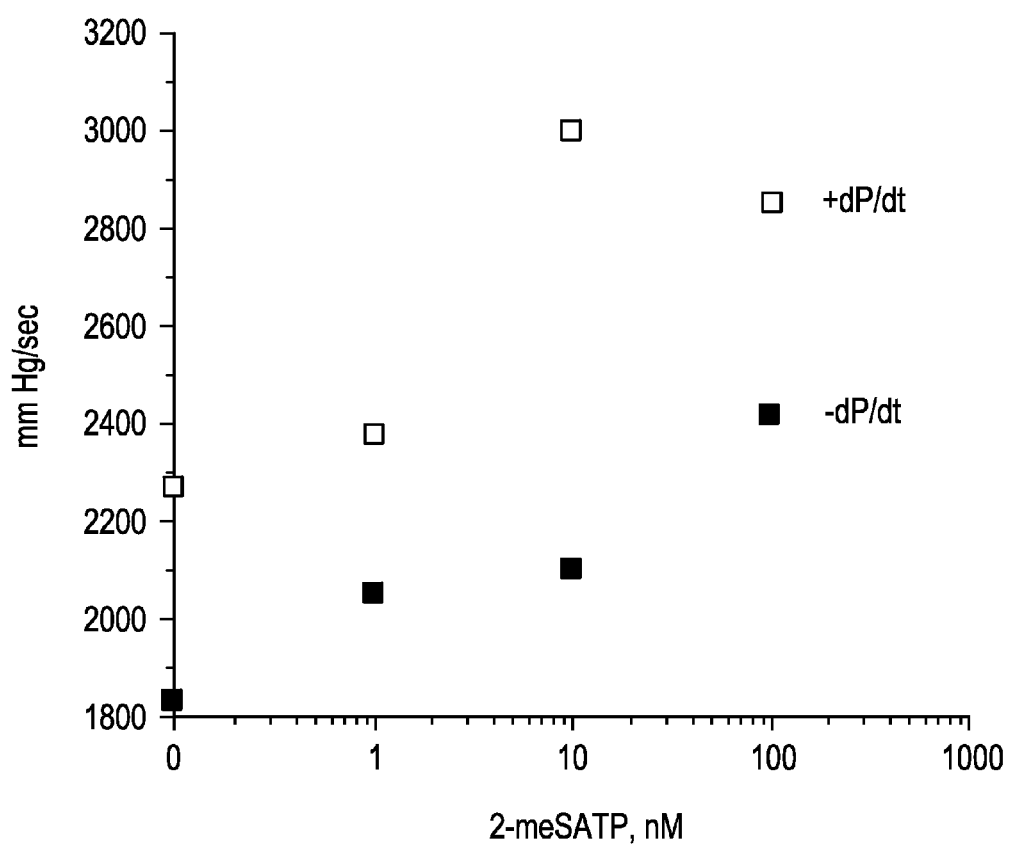

METHODS OF TREATING HEART FAILURE WITH MODIFIED ATP, ADP AND AMP COMPOUNDS

CROSS-REFERENCE TO RELATED APPLICATIONS

This application is a continuation of U.S. application Ser. No. 09/641,491, filed Aug. 18, 2000, now abandoned, which is a continuation-in-part of U.S. application Ser. No. 08/875,050, filed Sep. 23, 1997, now U.S. Pat. No. 6,255,292, which is a national phase application of PCT/US/96/03911, filed Mar. 22, 1996, which is a continuation-in-part of U.S. application Ser. No. 08/409,350, filed Mar. 23, 1995, now U.S. Pat. No. 5,712,258. The contents of each of the foregoing patent applications are incorporated herein by reference.

GOVERNMENT SUPPORT

The inventor has been supported by National Institute of Health Grants HL44188 and HL48225.

FIELD OF THE INVENTION

This invention relates to methods for treating heart failure, to methods for increasing cardiac muscle contractility, to methods for increasing cardiac muscle diastolic relaxation, to methods for increasing cellular contraction and to methods for increasing vasodilation.

BACKGROUND OF THE INVENTION

Positive inotropic agents (i.e., agents which increase the contractility of cardiac muscle in a dose dependent manner) find use, inter alia, in the treatment of congestive heart failure and as vasodialators. Representative of the three classes of positive inotropic agents are the $Na^+/K^+$ ATPase inhibitor digitalis, the β-adrenergic agonists dobutamine and dopamine, and the phosphodiesterase inhibitor amrinone.

Each of these classes of positive inotropic agents suffers from significant limitations. Digitalis displays a weak positive inotropic effect with a narrow therapeutic index, many adverse side effects, and undesirable interactions with other cardiac drugs. Dobutamine and dopamine cause desensitization of the β-adrenergic receptor-mediated positive inotropic response, are arrhythmogenic, and can only be administered intravenously. Orally active β-adrenergic agonists are only effective for a short period of time and lose efficacy due to desensitization. Phosphodiesterase inhibitors, such as milrinone, are potentially arrhythmogenic and have increased mortality relative to digitalis. ATP is known to cause an inotropic effect in the heart, which is thought to be mediated by the P2 purinergic receptor (P2PR).

Consequently, there is a need in the art for positive inotropic agents which overcome the disadvantages associated with known agents, as well as a need for further information on the mechanisms and receptors associated with cardiac muscle contractility.

OBJECTS OF THE INVENTION

It is one object of the present invention to provide inotropic agents, that is, compounds that modulate (i.e., increase or decrease) cardiac muscle contractility.

It is another object of the invention to provide methods for enhancing diastolic cardiac relaxation.

It is another object of the invention to provide methods of treating heart disease.

It is another object of the invention to provide positive inotropic agents.

It is a further object to provide positive inotropic agents that have a broader therapeutic index than those currently available.

It is yet another object to provide positive inotropic agents having longer and more evenly sustained rates of release than those currently available.

It is a further object to provide positive inotropic agents having longer duration of action than those currently available.

It is yet another object to provide inotropic agents that are orally active.

It is a another object of the invention to provide compounds having activity as vasodilators.

It is further object of the invention to provide methods for causing vasodilation.

SUMMARY OF THE INVENTION

These and other objects are accomplished by the present invention, which provides inotropic agents that are useful for the treatment of heart failure associated with, for example, myocardial infarction, rheumatic heart disease, infection of the myocardium, and viral infection of the heart. The methods of the present invention comprise the steps of identifying an animal, such as a mammal, in need of treatment for heart failure and administering to the animal a compound of formula XI in an amount effective to treat said heart failure.

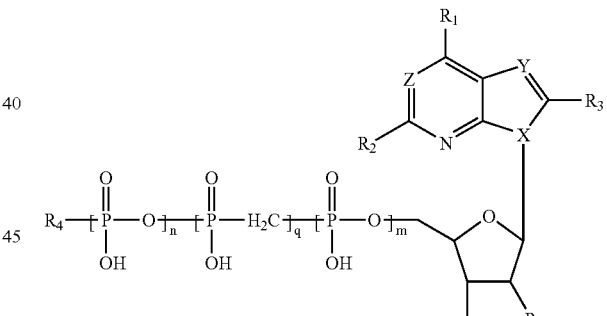

XI wherein $R_1$ is halogen or —$R_6$—$(R_7)_p$—$R_8$;

$R_2$ is hydrogen, alkyl, cycloalkyl, cycloalkenyl, alkynyl, alkylthio, aminoalkyl, halogen, or —$R_6$—$(R_7)_p$—$R_8$;

$R_3$ is H, halogen or —$R_6$—$(R_7)_p$—$R_8$;

$R_4$ is —$NH_2$, —OH or —SH;

$R_5$ is —OH or —$R_6$—$(R_7)_p$—$R_8$;

$R_6$ is —NH or —S $R_7$ is —$CH_2$ $R_8$ is H, $NH_2$, halogen, CN, CCH, cycloalkyl, having 3 to about 10 carbon atoms or aryl having 3 to about 20 carbon atoms $R_9$ is OH or acetamido;

X, Y, and Z are independently N or CH;

m is 0, 1, or 2;

n is 0 or 1;

q is 0 or 1, provided that at least one of m, n, and q is 1; and p is 0 to 10.

In certain embodiments of the present invention, the compound of Formula XI is one in which X, Y, and Z are N. In other embodiments, X and Y are N and Z is —CH.

According to one embodiment, q is 0 and the sum of m and n is 1; X, Y, and Z are N; and $R_2$ is $C_1$-$C_{10}$ alkyl, alkylthio, such as hexylthio, heptylthio, or undecylthio, alkynyl, cyanoalkylthio, cycloalkylthio or a substituted phenylalkylthio. In other embodiments $R_2$ is hexyl, ethynyl, cyanohexylthio, cyclohexylthio, or 4-aminophenylethylthio.

In still other embodiments of the present invention, q is 1 and the sum of m and n is 2; X, Y, and Z are N; and $R_2$ is an alkylthio, such as hexylthio.

In further embodiments, q is 0 and the sum of m and n is 3; X and Y are N; Z is CH or N; and $R_2$ is an alkylthio, such as methylthio or hexylthio, halogen, or H.

The sum of n, q, and m preferably is less than or equal to three and is at least 1. In preferred embodiments, n is 0, q is 0, and m is 2; n is 1, q is 0, and m is 2; n is 0, q is 0, and m is 1; or n is 0, q is 1, and m is 1. In certain preferred embodiments m is 1 or 2, q is 1, n is 0, and $R_4$ is OH. In other preferred embodiments m is 1, q is 0, n is 0, and $R_4$ is SH or OH. In further preferred embodiments m is 2, q is 0, n is 0, and $R_4$ is OH. In yet further preferred embodiments m is 1 or 2, q is 0, n is 0, and $R_4$ is $NH_2$.

In certain embodiments, the methods of the present invention utilize compounds having the following formula XII, or pharmaceutically acceptable salts thereof:

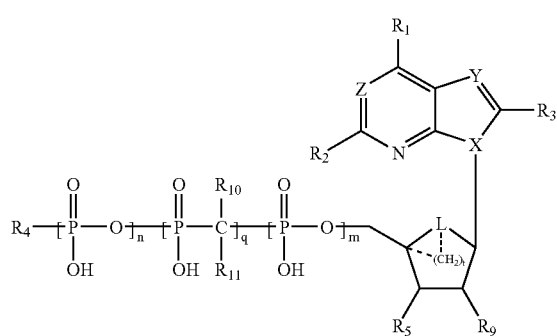

XII wherein L is O or CH; t is 0 or 1; and $R_{10}$ and $R_{11}$ are independently hydrogen or halogen, such as Cl, F, or Br; X, Y, and Z are N, and $R_2$ is thioalkyl or halogen, such as Cl. In preferred embodiments, the sum of n, q, and m is 3. The remaining substituents are defined as above.

The invention provides methods comprising the steps of identifying cardiac muscle tissue in need of increased muscle contractility and contacting the muscle tissue with compounds of formula XI and XII to increase muscle contractility. These methods optionally include measuring a rate of contraction associated with the muscle.

In a further embodiment, the present invention provides methods for identifying cardiac muscle tissue in need of increased diastolic relaxation and contacting the muscle tissue with compounds of formula XI and XII to increase diastolic relaxation.

The invention also provides methods for increasing cellular contraction in a mammalian cell comprising contacting a mammalian cell with compounds XI and XII and, optionally, measuring a rate of contraction associated with the cell.

BRIEF DESCRIPTION OF THE FIGURES

The numerous objects and advantages of the present invention can be better understood by those skilled in the art by reference to the accompanying figures, in which:

FIGS. 3a, 3b, 4a, and 4b show structure-activity relationship studies wherein $EC_{50}$ values determined for agonists stimulating myocyte contractility are compared to the $K_i$ of the same agonists in inhibiting high-affinity [$^{35}$S] ADPβS binding.

FIG. 10 shows the effects of P2 receptor and beta-adrenergic receptor agonists on the cardiac function of a work-performing mouse heart.

FIG. 11 shows the effects of 2-meSATP on cardiac contractility and diastolic relaxation in a working rat heart.

DETAILED DESCRIPTION OF THE INVENTION

Figure 1A:
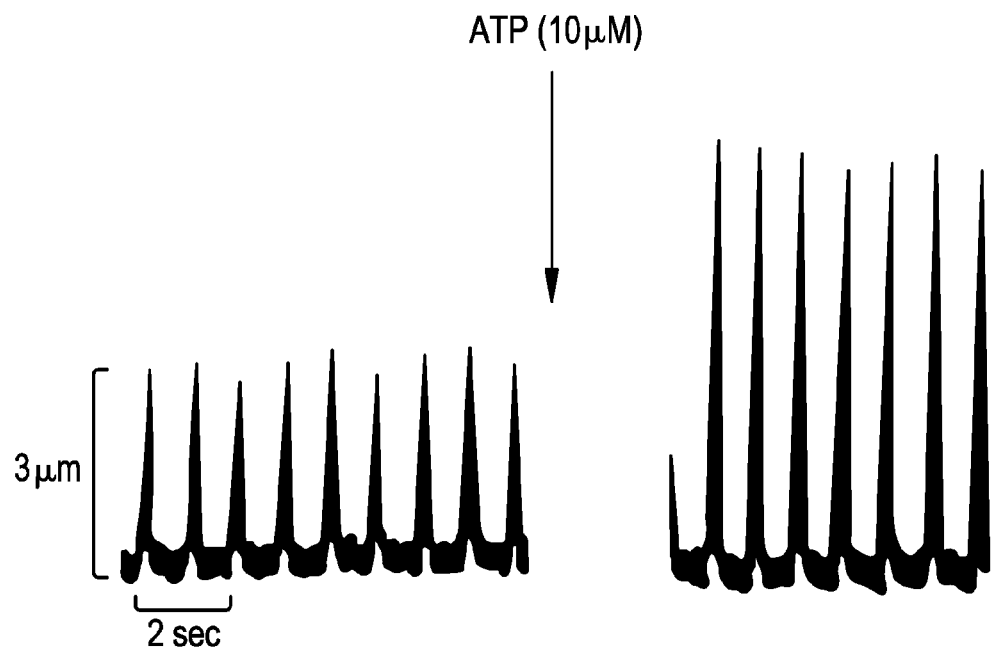
FIGS. 1a-1d show the positive inotropic response of cardiac ventricular myocytes to ATP and $P_2$ purinergic receptor agonists.
Figure 1B:
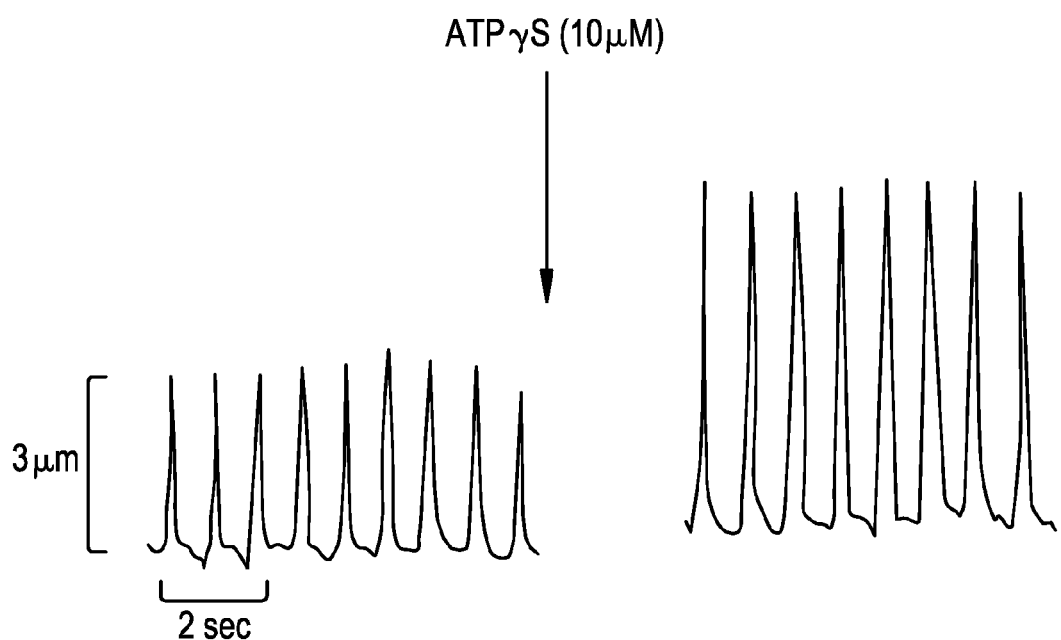
Figure 1C:
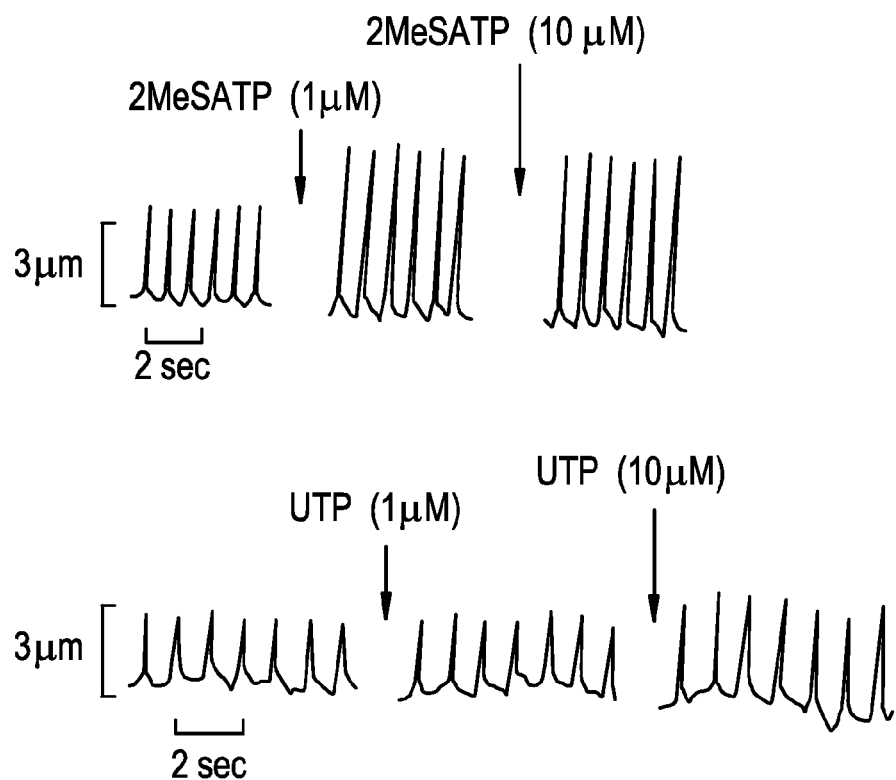
Figure 1D:
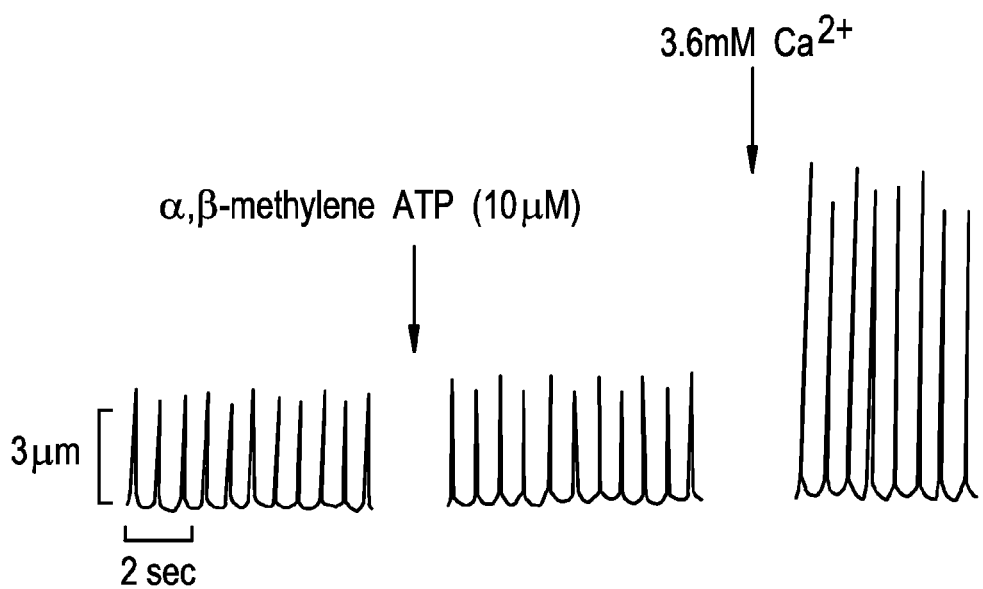

It has been found in accordance with the present invention that a class of purine-containing compounds act as inotropic agents and, moreover, as positive inotropic agents. These compounds are useful in methods of treating heart failure associated with, for example, myocardial infarction, rheumatic heart disease, infection of the myocardium, and viral infection of the heart. Additionally, these compounds are useful for enhancing cardiac performance by increasing cardiac muscle contractility and/or increasing diastolic cardiac muscle relaxation.

In certain embodiments, the compounds of the present invention have formula I or II:

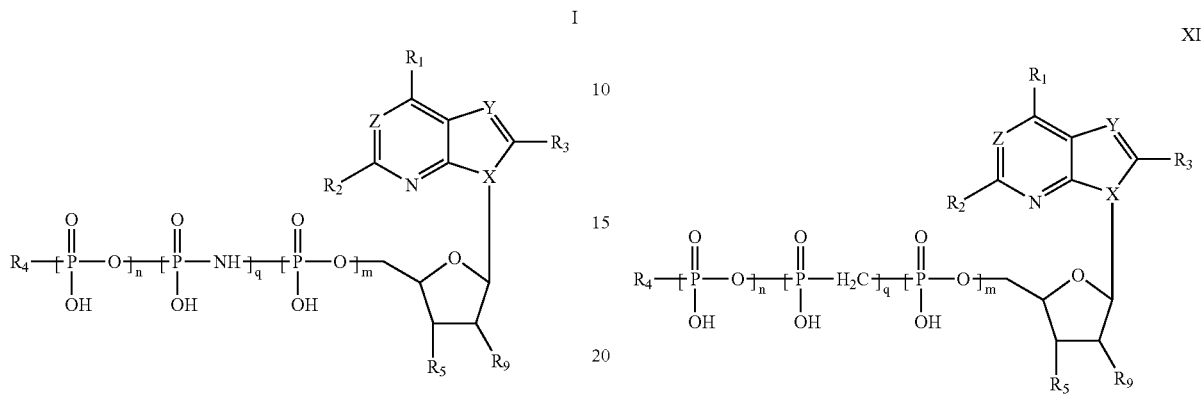

wherein:

$R_1$ and $R_2$, independently, are halogen or —$R_6$—($R_7$)$_p$—$R_8$;

$R_3$ is H, halogen or —$R_6$—($R_7$)$_p$—$R_8$;

$R_4$ is OH, SH or $NH_2$;

$R_5$ is OH or acetamido;

$R_6$ is NH or S;

$R_7$ is alkylene having from 1 to 10 carbon atoms;

$R_8$ is H, $NH_2$, CN, cycloalkyl having 3 to about 10 carbon atoms, or aryl having 3 to about 20 carbon atoms;

X and Y are independently N or CH;

n is 0 or 1;

q is 0 or 1;

m is 1 or 2; and p is 0 or 1.

In certain preferred embodiments $R_8$ is —$C_6H_{11}$, —$C_5H_9$, —$C_6H_5$, —$C_6H_4$—$NO_2$, or —$CH[C_6H_4(CH_3)][C_6H_3$ $(OCH_3)_2]$. In other preferred embodiments $R_3$ is H, and $R_1$ and $R_2$ are $NH_2$, S or Cl, and in further preferred embodiments X and Y are N or CH.

In other embodiments, compounds of the invention have the formula XI:

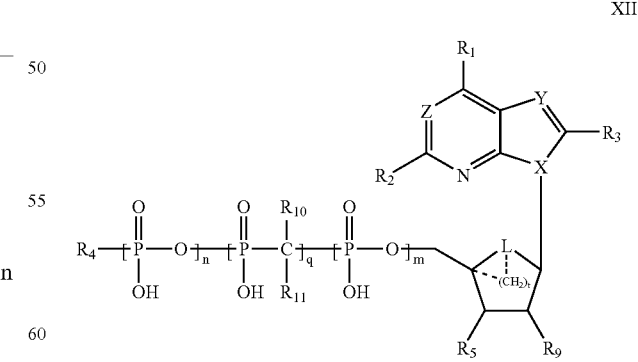

wherein $R_1$ is halogen or —$R_6$—($R_7$)$_p$—$R_8$;

$R_2$ is hydrogen, alkyl, cycloalkyl, cycloalkenyl, alkynyl, alkylthio, aminoalkyl, alkylthio, alkylamino, halogen, or —$R_6$—($R_7$)$_p$—$R_8$;

$R_3$ is H, halogen or —$R_6$—($R_7$)$_p$—$R_8$;

$R_4$ is —OH or —SH;

$R_5$ is —OH or —$R_6$—($R_7$)$_p$—$R_8$;

$R_6$ is NH or S $R_7$ is $CH_2$ $R_8$ is H, halogen, CN, CCH, cycloalkyl, having 3 to about 10 carbon atoms or aryl having 3 to about 20 carbon atoms;

$R_9$ is OH or acetamido;

X, Y, and Z are independently N or CH;

m is 0, 1, or 2;

n is 0 or 1;

q is 0 or 1; and p is 0 to 10.

In further preferred embodiments, compounds used in the methods of the present invention utilize compounds having the following formula XII:

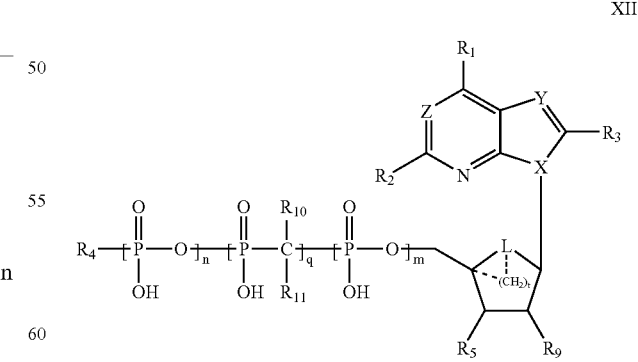

wherein

L is CH or O;

t is 0 or 1;

$R_1$ is halogen or —$R_6$—($R_7$)$_p$—$R_8$;

$R_2$ is hydrogen, alkyl, cycloalkyl, cycloalkenyl, alkynyl, alkylthio, aminoalkylthio, halogen, or $-R_6-(R_7)_p-R_8$;

$R_3$ is H, halogen or $-R_6-(R_7)_p-R_8$;

$R_4$ is $-OH$ or $-SH$;

$R_5$ is $-OH$ or $-R_6-(R_7)_p-R_8$;

$R_6$ is NH or S;

$R_7$ is $CH_2$;

$R_8$ is H, $NH_2$, halogen, CN, CCH, cycloalkyl, having 3 to about 10 carbon atoms or aryl having 3 to about 20 carbon atoms;

$R_9$ is OH or acetamido;

$R_{10}$ and $R_{11}$ are independently H or halogen;

X, Y, and Z are independently N or CH;

m is 0, 1, or 2;

n is 0 or 1;

q is 0 or 1, provided that at least one of n, q, and m is 1; and p is 0 to 10.

In certain embodiments of the present invention, compounds have the formula XI wherein $R_3$ is H. In further embodiments, X, Y, and Z are each N; $R_1$ is $NH_2$; $R_5$ and $R_9$ are $-OH$; $R_3$ is H; n is 1, q is 0 and m is 0; and $R_2$ is selected from alkylthio, alkyl, alkynyl, cyanoalkylthio, cycloalkylthio, and aminoarylalkylthio. $R_2$, preferably, is hexylthio, hexyl, ethynyl, cyanohexylthio, cyclohexylthio or 4-aminophenylethylthio AMP.

In other embodiments of the present invention, the compounds have the formula XI wherein X and Y are N and Z is CH or N; $R_1$ is $NH_2$, $R_3$ is H; n is 1, q is 0, and m is 2; and $R_2$ is alkylthio, Cl, or H.

In other embodiments, compounds of the present invention have formula XI and include an α, β methylene triphosphate group in the side chain of the sugar moiety or a β, γ-methylene triphosphate group in the side chain of the sugar moiety. Such sugar moieties can be 2'-substituted, 2'-deoxy or 3'-substituted, 3'-deoxy moieties.

In certain embodiments, compounds of formula XII preferably have t=1 and L=CH. In other embodiments, t=0 and L=CH. Preferably, the sum of m, q and n is 3; X, Y, and Z are N; and $R_2$ is alkylthio or halogen.

Alkyl groups according to the invention include but are not limited to straight chain and branched chain hydrocarbons such as methyl, ethyl, propyl, butyl, pentyl, hexyl, heptyl, octyl, nonyl, decyl, undecyl, dodecyl, isopropyl, 2-butyl, isobutyl, 2-methylbutyl, isopentyl, 2-methylpentyl, 3-methylpentyl, 2-ethylhexyl and 2-propylpentyl groups having 1 to about 20 carbon atoms, preferably having about 3 to 10. Cycloalkyl groups are cyclic alkyl groups such as cyclopropyl, cyclopentyl and cyclohexyl groups preferably having about 3 to 20 carbon atoms. Alkylene groups are straight chain or branched chain hydrocarbons that are covalently bound to two other groups. Preferred alkylene groups have the formula $-(CH_2)_n-$ where n is 1 to about 12, preferably 1 to about 6, including methylene (n=1) and ethylene (n=2) groups. The alkyl, cycloalkyl and alkylene groups of the invention can be substituted with a wide variety of moieties and/or internally interrupted with heteroatoms, such as O, N, or S.

Aryl groups according to the invention are aromatic groups having 3 to about 20 carbon atoms, preferably from 3 to about 10 carbon atoms, including, for example, benzyl, imidazolyl, naphthyl, phenyl, pyridyl, pyrimidinyl, and xylyl groups and substituted derivatives thereof, particularly those substituted with alkyl, alkoxy, amino, and nitro groups.

The term halogen as used herein is intended to denote substituents derived from fluorine, chlorine, bromine, or iodine.

Preferred groups having formula $-R_6-(R_7)_p-R_8$ include the following: $-NH_2$, $-NH-CH_3$, $-NH-C_2H_5$, $-S-CH_3$, $-NH-CH_2-NH_2$, $-NH-(CH_2)_2-NH_2$, $-NH-(CH_2)_3-NH_2$, $-NH-(CH_2)_4-NH_2$, $-NH-(CH_2)_5-NH_2$, $-NH-(CH_2)_6-NH_2$, $-S-(CH_2)_6-CN$, $-S-CH_2-C_6H_4-NO_2$, $-S-(CH_2)_2-C_6H_4-NO_2$, $-S-CH_2-CN$, $-S-(CH_2)_2-CN$, $-S-(CH_2)_3-CN$, $-S-(CH_2)_4-CN$, $-S-(CH_2)_5-CN$, $-NH-C_6H_5$, $-NH-CH_2-C_6H_5$, $-NH-(CH_2)_2-C_6H_5$, $-NH-(CH_2)_3-C_6H_5$, $-NH-(CH_2)_4-C_6H_5$, $-NH-(CH_2)_5-C_6H_5$, $-NH-(CH_2)_6-C_6H_5$, $-NH-C_6H_{11}$, $-NH-C_5H_9$, $-NH-CH_2-CH[C_6H_4(CH_3)][C_6H_3(OCH_3)_2]$, $-NH-CH_2C_6H_4-NH_2$.

While not wishing to be bound by a particular theory, the compounds of the invention are believed to exert their positive inotropic effect by mechanisms different from those of other known positive inotropic agents. This mechanism is believed to involve binding to a novel $P_2$-like purinergic receptor. As used herein, a $P_2$-like purinergic receptor is one which upon activation leads to an increase in calcium entry and myocyte contractility subsequent to the activation of a novel mechanism.

The compounds of the present invention also possess utility as vasodilators. As used herein, the term "vasodilator" is given its accepted meaning of a compound or other agent which causes (i.e., induces or initiates) vasodilation, which is the widening of the lumen of blood vessels.

The vasodilators of the invention can be employed as the sole active agent in a pharmaceutical or can be used in combination with other active ingredients, e.g., other vasodilators or adjuvants useful in the treatment of diseases or disorders.

The compounds of the invention contain amino groups and, therefore, are capable of forming salts with various inorganic and organic acids. Such salts are also within the scope of this invention. Representative salts include inorganic addition salts such as phosphate, hydrochloride, hydrobromide, hydroiodide, hemisulfate, sulfate, bisulfate and nitrate, and organic salts including, for example, acetate, benzoate, butyrate, citrate, fumarate, heptanoate, hexanoate, lactate, maleate, succinate and tartrate. The salts can be formed by conventional means, such as by reacting the free base form of the product with one or more equivalents of the appropriate acid in a solvent or medium in which the salt is insoluble, or in a solvent such as water which is later removed in vacuo or by freeze drying. The salts also can be formed by exchanging the anions of an existing salt for another anion on a suitable ion exchange resin.

The present invention also provides prophylactic, diagnostic, and therapeutic compositions comprising one or more compounds of the invention. By administering an effective amount of such compositions, for example, prophylactic or therapeutic responses can be produced in a human or some other type mammal. It will be appreciated that the production of prophylactic or therapeutic responses includes the initiation or enhancement of desirable responses, as well as the cessation or suppression of undesirable responses.

According to certain embodiments of the present invention, methods are provided for enhancing cardiac performance in a mammal. This can be accomplished by increasing cardiac muscle contractility and/or increasing diastolic relaxation in cardiac muscle tissue.

Compositions of the invention can be administered in unit dosage form and may be prepared by any of the methods well known in the pharmaceutical art, for example, as described in *Remington's Pharmaceutical Sciences* (Mack Pub. Co., Easton, Pa., 1980), herein incorporated by reference. The compositions can be in the form of a solid, semisolid or liquid form and can include one or more of the compounds of the invention as an active ingredient in admixture with an organic or inorganic carrier or excipient suitable, for example, for oral administration, parenteral administration, intranasally or dermally, via, for example, trans-dermal patches. Other suitable modes of administration will be apparent to those skilled in the art. The active ingredient can be compounded, for example, with the usual non-toxic, pharmaceutically acceptable carriers for tablets, pellets, capsules, suppositories, solutions, emulsions, suspensions, and any other form suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparations, in solid, semisolid, or liquid form, and in addition auxiliary, stabilizing, thickening and coloring agents and perfumes maybe used. The active ingredient is included in the pharmaceutical composition in an amount sufficient to produce the desired effect upon the process or condition of diseases.

For oral administration, tablets containing various excipients such as microcrystalline cellulose, sodium citrate, calcium carbonate, dicalcium phosphate and glycine may be employed along with various disintegrants such as starch and preferably corn, potato or tapioca starch, alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, glycerin and various like combinations thereof.

For parenteral administration, solutions containing the compounds of the invention in either sesame or peanut oil or in aqueous propylene glycol can be employed. The aqueous solutions should be suitably buffered (preferably pH>8) if necessary and the liquid diluent first rendered isotonic. These aqueous solutions are suitable for intravenous injection purposes. The oily solutions are suitable for intra-articular, intramuscular and subcutaneous injection purposes. The preparation of all these solutions under sterile conditions is readily accomplished by standard pharmaceutical techniques well-known to those skilled in the art. Additionally, it is possible to administer the compounds of the present invention topically when treating inflammatory conditions of the skin and this may preferably be done by way of creams, jellies, gels, pastes, ointments and the like, in accordance with standard pharmaceutical practice.

The inotropic agents of the invention can be employed as the sole active agent in a pharmaceutical or can be used in combination with other active ingredients, e.g., other positive inotropic agents useful in diseases or disorders.

The amount of active ingredient that may be combined with the carrier materials to produce a single dosage form will vary depending upon the host treated and the particular mode of administration. The specific dose level for any particular patient will depend on a variety of factors including the activity of the specific compound employed, the age, body weight, general health, sex, diet, time of administration, route of administration, rate of excretion, drug combination, and the severity of the particular disease undergoing therapy. In some instances, dosage levels below the lower limit of the aforesaid range may be more than adequate, while in other cases still larger doses may be employed without causing any harmful side effects provided that such higher dose levels are first divided into several small doses for administration throughout the day. The concentrations of the compounds described herein found in therapeutic compositions will vary depending upon a number of factors, including the dosage of the drug to be administered, the chemical characteristics (e.g., hydrophobicity) of the compounds employed, and the route of administration. In general terms, the compounds of this invention may be provided in an aqueous physiological buffer solution (for example, 1 cc) containing about 0.2% w/v compound for oral administration. Typical dose ranges are from about 285 µg/kg of body weight per day in three divided doses; a preferred dose range is from about 42 µg/kg to about 171 µg/kg of body weight per day. The preferred dosage of drug to be administered is likely to depend on such variables as the type and extent of progression of the disease or disorder, the overall health status of the particular patient, the relative biological efficacy of the compound selected, and formulation of the compound excipient, and its route of administration, as well as other factors, including bioavailability, which is in turn influenced by several factors. For example, if the compound is metabolized in the liver or excreted in bile, some of the active compound absorbed from the gastrointestinal tract will be inactivated by the liver before it can reach the general circulation and be distributed to its sites of action. It is not believed that the compounds of the invention will be subject to this first-pass loss. Additionally, because the instant compounds are polar and water soluble, it is expected that they will have a small volume of distribution, and thus be readily eliminated by the kidney. Moreover, binding of the instant compounds to plasma proteins may limit their free concentrations in tissues and at their locus of action since it is only the unbound drug which equilibriums across the membrane receptor sites. It is anticipated that the phosphate moiety of the instant compounds may facilitate binding of the compounds to plasma albumins, which will in turn influence the amount of free compound available to activate muscle cell P2 purinergic receptors. However, it is expected that such binding to plasma protein will not generally limit renal tubular secretion of biotransformation since these processes lower the free drug concentration and this is rapidly followed by the association of this drug-protein complex. Another factor affecting bioavailability is the distribution of the compounds to tissues. Given the relatively small size of the compounds and their water solubility, it is anticipated that the compounds will have a relatively fast second phase of drug distribution. This distribution is determined by both the blood flow to the particular tissue of the organ, such as the heart, as well as the rate at which the compounds diffuse into the interstitial compartment from the general circulation through the highly permeable capillary endothelial (except in the brain). Due to the relative hydrophilicity of these compounds, it is anticipated that there will be no fat or other significant tissue reservoir of the compounds which would account for a third phase of distribution-accumulation.

Calculation of the above dosages are based on the molecular weight of the compounds, which range from 500-1000 gram per mole, and upon in vitro determinations of $K_d$ values for the compounds for the P2 purinergic receptors, which range from 30-100 nM. For example, assuming a volume of distribution of 15-20 liters for a 70 kg subject, a Kd of 100 nM, and a volume of distribution of 20 liters, a 2 mg loading dose would be required to achieve the Kd value in the extracellular fluid compartment. The typical and preferred dose ranges were then calculated based on all the variables as well as the factors discussed above.

In certain embodiments, methods according to the invention involve contacting compounds having formula I, II, XI, or XII with cardiac muscle tissue. As used herein, the term "contacting" means directly or indirectly causing placement together of moieties to be contacted, such that the moieties come into physical contact with each other. Contacting thus includes physical acts such as placing the moieties together in a container, or administering moieties to a patient.

The compounds of the invention also can be used as research reagents. The compounds, for example, can be used as synthetic intermediates in the preparation of nucleosides, nucleotides, and oligonucleotides. For example, the compounds of the invention can be functionalized as phosphoramidites and used in automated oligonucleotide syntheses such as those associated with the well-known polymerase chain reaction (PCR) procedure.

The invention also includes receptor polypeptides (e.g., $P_2$-like receptor polypeptides) from any naturally occurring source, preferably mammalian, more preferably human, which exhibit biological activity. In the context of the invention, biological activity includes binding to a compound of the invention or otherwise interacting with such a compound to facilitate or ultimately produce an inotropic response. Polypeptides also include homologous sequences (as defined below); allelic variations; natural mutants; induced mutants; proteins encoded by DNA which hybridizes under high or low stringency conditions to receptor encoding nucleic acids retrieved from naturally occurring material; and polypeptides or proteins retrieved by antisera to the $P_2$-like receptor, especially by antisera to the active site or binding domain of the $P_2$-like receptor. The invention also provides other polypeptides, e.g., fusion proteins, which include $P_2$-like receptor polypeptides or biologically active fragments thereof.

$P_2$-like receptor polypeptides will generally exhibit at least about 70%, more preferably about 80%, more preferably 90%, still more preferably 95%, or even 99%, homology (as defined herein) with all or part of a naturally occurring $P_2$-like receptor sequence. For the purposes of determining homology the length of comparison of sequences will generally be at least 8 amino acid residues, usually at least about 20 amino acid residues, more usually at least about 24 amino acid residues, typically at least 28 amino acid residues, and preferably more than about 35 amino acid residues.

The present invention also provides for analogs of $P_2$-like receptor polypeptides. Analogs can differ from naturally occurring $P_2$-like receptor polypeptides by amino acid sequence differences or by modifications which do not affect sequence, or by both.

Modifications (which do not normally alter primary sequence) include in vivo or in vitro chemical derivatization of polypeptides, e.g., acetylation, or carboxylation. Also included are modifications of glycosylation, e.g., those made by modifying the glycosylation patterns of a polypeptide during its synthesis and processing or in further processing steps. Representative modifications include exposing the polypeptide to enzymes which affect glycosylation, such as mammalian glycosylating or deglycosylating enzymes. Also embraced are sequences which have phosphorylated amino acid residues, e.g., phosphotyrosine, phosphoserine, or phosphothreonine.

Included are peptides which have been modified so as to improve their resistance to proteolytic degradation or to optimize solubility properties. Analogs can differ from naturally occurring $P_2$-like receptor polypeptides by alterations of their primary amino acid sequence. These peptides include genetic variants, both natural and induced. Induced mutants can be made by various techniques, e.g., by random mutagenesis of the encoding nucleic acids using irradiation or exposure to ethanemethylsulfate (EMS), or by site-specific mutagenesis or other techniques of molecular biology. See, Sambrook, Fritsch and Maniatis (1989), Molecular cloning: A Laboratory Manual (2d ed.), CSH Press. Also included are analogs which include residues other than naturally occurring L-amino acids, e.g., D-amino acids or non-naturally occurring or synthetic amino acids such as β- or γ-amino acids. The peptides of the invention are not limited to products of any of the specific exemplary process listed herein.

In addition to substantially full-length polypeptides, the present invention provides biologically active fragments of the polypeptides. A $P_2$-like receptor polypeptide (or fragment) is biologically active if it exhibits a biological activity of a naturally occurring $P_2$-like receptor polypeptide. Such biological activities include the ability to bind, e.g., specifically bind, a compound of the invention. The affinity of a receptor polypeptide fragment for a positive inotropic agent of the present invention preferably is at least 1% of (more preferably at least 10% or, yet more preferably at least 50% of, still more preferably at least equal to) the affinity of a naturally occurring receptor polypeptide for a compound of the invention). Another biological activity is the ability to bind to an antibody which is directed at an epitope which is present on a naturally occurring $P_2$-like receptor, preferably an epitope on a $P_2$-like receptor domain of naturally occurring $P_2$-like receptor.

Putative biologically active fragments of $P_2$-like receptors can be generated by methods known to those skilled in the art. The ability of a candidate fragment to bind a positive inotropic agent of the invention can be assessed by methods known to those skilled in the art.

The invention also provides nucleic acid sequences, and purified preparations thereof, which encode the $P_2$-like receptor polypeptides described herein.

The invention also provides antibodies, preferably monoclonal antibodies, which bind specifically to $P_2$-like receptor polypeptides and preferably antibodies which bind to the agonist binding domain of a $P_2$-like receptor polypeptide.

As used herein, the term "fragment or segment", as applied to a polypeptide, will ordinarily be at least about 5 contiguous amino acids, typically at least about 10 contiguous amino acids, more typically at least about 20 contiguous amino acids, usually at least about 30 contiguous amino acids, preferably at least about 40 contiguous amino acids, more preferably at least about 50 contiguous amino acids, and even more preferably at least about 60 to 80 or more contiguous amino acids in length.

As used herein, the term "substantially pure" describes a compound (e.g., a protein or polypeptide such as a $P_2$-like receptor protein or polypeptide) which has been separated from components which naturally accompany it. Typically, a compound is substantially pure when at least 10%, more preferably at least 20%, more preferably at least 50%, more preferably at least 60%, more preferably at least 75%, more preferably at least 90%, and even more preferably at least 99%, of the total material (by volume, by wet or dry weight, or by mole percent or mole fraction) in a sample is the compound of interest. Purity can be measured by any appropriate method. In the case of polypeptides, for example, purity can be measured by column chromatography, polyacrylamide gel electrophoresis, or HPLC analysis. A compound such as a protein is also substantially purified when it is essentially free of naturally associated components or when it is separated from the native contaminants which accompany it in its natural state.

A "substantially pure nucleic acid", as used herein, refers to a nucleic acid sequence, segment, or fragment which has been purified from the sequences which flank it in a naturally occurring state, e.g., a DNA fragment which has been removed from the sequences which are normally adjacent to the fragment such as the sequences adjacent to the fragment and Sen, L., Liang, B. T., Colucci, W. S., Smith, T. W., *Circ. Res.* 67:1182-1192 (1990), modified to include the use of a high-speed peristaltic pump (Masterflex from Cole-Palmer/Spectrum), choice of lots of collagenase, hyaluronidase and protease that give the highest proportion of rod-shaped myocytes, inclusion of bovine serum albumin containing various enzymes, and pre-plating with laminin-coated plates or glass coverslips (for contractility measurement) to eliminate damaged, rounded up myocytes. Specifically, hearts from Sprague-Dawley rats were perfused in a retrograde manner for 5 minutes in Krebs-Henseleit (KH) bicarbonate buffer containing 118 mM NaCl, 4.6 mM KCl, 1.2 mM $MgSO_4$, 1.25 mM $CaCl_2$, 1.2 mM $KH_2PO_4$, 25 mM $NaHCO_3$, and 11 mM glucose, gassed with 95% $O_2$/5% $CO_2$/at pH 7.4 (37° C., and an osmolality of 287 mosm/liter). The perfusion buffer was changed to nominally $Ca^{2+}$-free KH buffer for 5 min to arrest spontaneous beating. The heart was then perfused with the $Ca^{2+}$-free KH buffer containing 0.05% collagenase (Worthington) and 0.03% hyaluronidase (Sigma Chem. Co., St. Louis, Mo.) for 20 min. After removing the atria and the great vessels, the ventricular tissue was finely minced in the same collagenase/hyaluronidase buffer described above except that trypsin (0.02 mg/ml, Sigma) and deoxyribonuclease (0.02 mg/ml, Sigma) was also added. The minced tissue was further incubated in this buffer at 37° C. with shaking to facilitate dissociation of individual ventricular myocytes. The dissociated cells containing some damaged cells were filtered and layered twice over a 6% bovine serum albumin gradient. The rod-shaped healthy heart cells sedimented more easily than the round damaged cells. After the second sedimentation through the 6% BSA gradient, the final pellet contains more than 90% rod-shaped heart cells.

B. Cardiac Cell Preparation

Ventricular myocytes were cultured from chick embryos 14 days in ovo according to known procedures. Briefly, isolated ventricular myocytes from chick embryos 14 in ovo were prepared in calcium- and magnesium-free Hanks' balanced salt sodium (HBSS) containing 0.025% trypsin (GIBCO, Grand Island, N.Y.). After neutralization of trypsin medium containing horse serum and HBSS, cells were centrifuged and resuspended in culture medium containing 6% fetal bovine serum, 40% Medium 199 (GIBCO), 0.1% penicillin/streptomycin, and a salt solution. The final concentrations in the culture medium (in mmol/L) were Na 142, K 3.3, Mg 0.7, Ca 1.4, Cl 130, $HCO_3$ 16.4, and glucose 5.5. Cells were plated at a density of 400,000 cell per ml and cultivated in a humidified 5% $CO_2$-95% in a genome in which it naturally occurs. The term also applies to nucleic acids which have been substantially purified from other components which naturally accompany the nucleic acid, e.g., RNA or DNA, which has been purified from proteins which naturally accompany it in the cell.

"Homologous", as used herein, refers to the subunit sequence similarity between two polymeric molecules, e.g., between two nucleic acid molecules such as two DNA molecules, or two polypeptide molecules. When a subunit position in both of the two molecules is occupied by the same monomeric subunit (e.g., if a position in each of two DNA molecules is occupied by adenine) then they are homologous at that position. The homology between two sequences is a direct function of the number of matching or homologous positions. For example, if 5 of 10 positions in two compound sequences are matched or homologous then the two sequences are 50% homologous, if 9 of 10 are matched or homologous, the two sequences share 90% homology. By way of example, the DNA sequences 3' ATTGCC 5' and 3' TTTCCG 5' share 50% homology.

Complex or affinity complex, as used herein, refers to an association of a first and a second component, e.g., a receptor and its ligand. The association can include either or both covalent and noncovalent bonds.

Thus, the invention provides a novel receptor capable of binding the inotropic agents of the invention.

Additional objects, advantages, and novel features of this invention will become apparent to those skilled in the art upon examination of the following examples thereof, which are not intended to be limiting.

EXAMPLE 1

Demonstration of a Positive Inotropic Response of Cardiac Ventricular Myocytes to ATP and $P_2$ Purinergic Receptor Agonists Cardiac ventricular myocytes were prepared and changes in the contractile amplitude were determined in response to the agonist(s).

A. Cell Isolation Procedure

The cell isolation procedure was generally that of Kelly, R. A., Eid, H., Kramer, B. K., O'Neill, M., Liang, B. T., Reers, M., Smith, T. W., *J. Clin. Invest.* 86:1164-1171 (1990), air mix at 37° C. Cells became confluent on day 3 in culture and contractility measurement was carried out on that day.

C. Determination of Contractile Amplitude

Measurement of contractile amplitude in cultured ventricular cells was carried out generally according to the methods of Xu, D., Kong, H., Liang, B. T., *Circ. Res.* 70:56-65 (1992), and Barry, W. H., and Smith, T. W., *J. Physiol.* (Lond) 325:243-260 (1982). Ventricular myocytes became adhered to coverslips at the bottom of the dish during culturing, and exhibited spontaneous rhythmic beating by day 3 of culturing. Coverslips containing beating cells were placed in a perfusion chamber situated on the stage of an inverted phase-contrast microscope (Nikon) with an inlet and an outlet which allowed infusion and removal of medium containing the various adenosine analogs. The contractile amplitude of the cultured cell was determined by an optico-video motion detection system with a video motion analyzer (Colorado Video, Boulder, Colo.) as previously described. The perfusion medium contained the various adenosine analogs indicated as well as the following components (mmol/L): HEPES 4 (pH=7.4), NaCl 137, KCl 3.6, $MgCl_2$ 0.5, $CaCl_2$ 0.6, glucose 5.5 horse serum at 6%.

Measurement of contractile amplitude was carried out on only one cell per coverslip and each culture dish contained 5 coverslips. After achieving a steady state of beating in medium without adenosine analogs, the medium was switched to that containing the indicated adenosine drugs. Both the basal contraction amplitude and the amplitude measured during adenosine analog exposure were determined. The stimulatory effect of the various adenosine analogs on the contractile state was predominantly on the amplitude of contraction (see Xu, D., Kong, H., and Liang, B. T., supra). The basal rate of contraction was 105±16, n=311, ±S.D. There was no significant consistent effect of any of the analogs on the spontaneous rate of contraction.

It can be seen from FIGS. 1a-1d that the $P_2$ agonist 2-methylthio ATP was capable of stimulating an increase in contractile amplitude, and that $P_{2x}$ ($\alpha,\beta$-methylene ATP) and $P2_u$ (UTP) agonists were not capable of producing the same effect. These data indicate that a $P_2$-like receptor is responsible for mediating a positive inotropic response.

EXAMPLE 2

Intact Myocyte Binding with the $P_2$-selective Radioligand [$^{35}$S] 5'-O-2-thiodiphosphate ([$^{35}$S] ADPβS)

Cardiac ventricular myocytes were prepared and incubated with progressively increasing concentrations of [$^{35}$S] ADPβS. The binding reaction is performed by the addition of a Dulbecco's Modified Eagle's Medium (which contains 1-glutamine and glucose but lacks phenol red, adenosine nucleotides, and sodium bicarbonate, buffered by HEPES, pH=7.4) containing [$^{35}$S]ADPβS (0.5 to 200 nM, for saturation isotherm study). Nonradioactive ADPβS is used to define the level of nonspecific binding. Additional purinergic agonists or antagonists are added depending on the experimental conditions. Following a 30-minute incubation at 37° C., cells are washed three times with 3 ml of ice-cold wash buffer (containing 120 mM NaCl, 5.4 mM KCl, 0.8 mM $MgSO_4$, 1.8 mM $CaCl_2$, 50 mM HEPES, and 1.0 mM $NaH_2PO_4$ adjusted to pH=7.4). One ml of 0.5 M NaOH is added to the monolayer culture to solubilize the cell protein and 0.5 ml of Tris buffer, pH=7.4 is added to neutralize NaOH prior to scintillation counting for $^{35}$S.

To determine the $B_{max}$ and $K_d$ of the specific [$^{35}$S]ADPβS binding, a computer-aided nonlinear regression analysis (LIGAND PROGRAM) is used. See, *Annals of Biochemistry* 1980, 107, 220-239. Both a one-site and a two-site model is applied to fit the data points. The data indicate that [$^{35}$S] ADPβS labelled both high- and low-affinity sites in the intact myocyte binding and that over the range of 0.5 to 12 nM, the radioligand labels the high-affinity sites with a linear Scatchard plot; whereas over the range of 150-150 nM, a low-affinity site ($K_d$=40 nm) is labeled which has a high $B_{max}$ (in the range of 1000 fmole per mg of total cellular proteins).

Figure 2A:
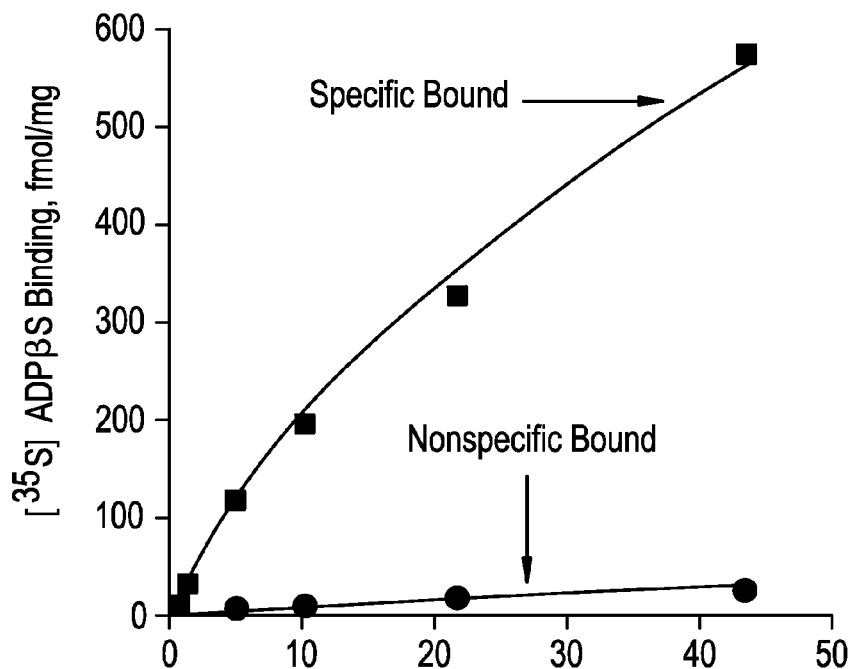
FIGS. 2a and 2b show intact myocyte binding with the $_{P2}$-selective radioligand [$^{35}$S] ADPβS.
Figure 2B:
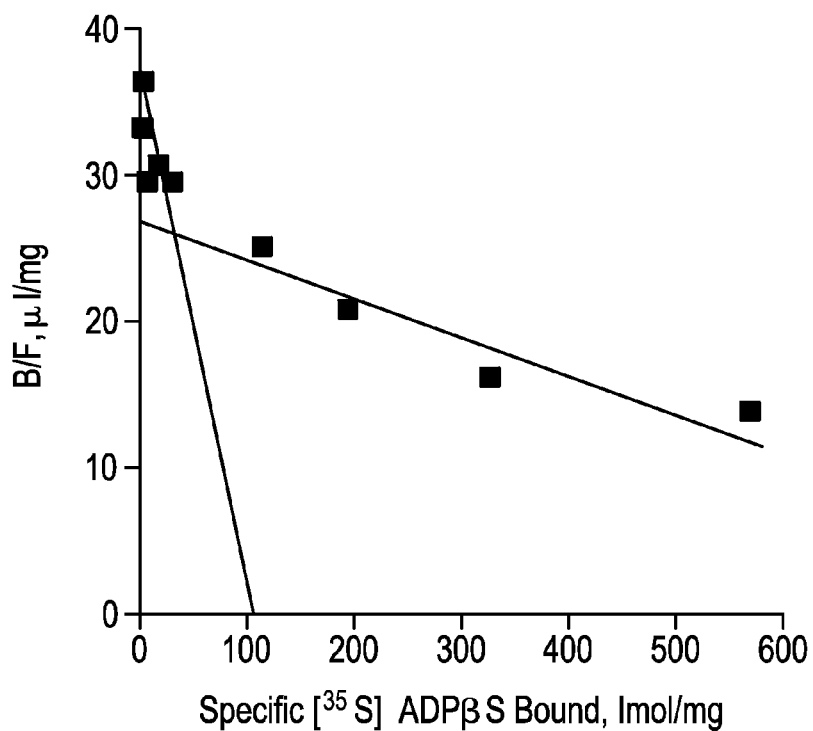

FIG. 2a represents a saturation isotherm of [$^{35}$S] ADPβS binding to intact myocytes and FIG. 2b shows a Scatchard transformation of the data in FIG. 2a. The low affinity and high affinity binding sites for [$^{35}$S] ADPβS are readily seen. Three lines of evidence exist which indicate that the high-affinity sites mediate the positive inotropic response: (1) the order of potency of various agonists in causing the positive inotropic effect is similar to the order of potency of the same agonists in competing against the high-affinity [$^{35}$S] ADPβS sites; (2) the desensitization of the positive inotropic effect of ATP agonists is correlated with the disappearance of the high-affinity [$^{35}$S] ADPβS sites; and (3) the $EC_{50}$ values of the agonists in producing the positive inotropic effect are similar to the Ki values of the same agonists in competing with the high-affinity [$^{35}$S] ADPβS sites.

EXAMPLE 3

Structure-Activity Relationships

Figure 3B:
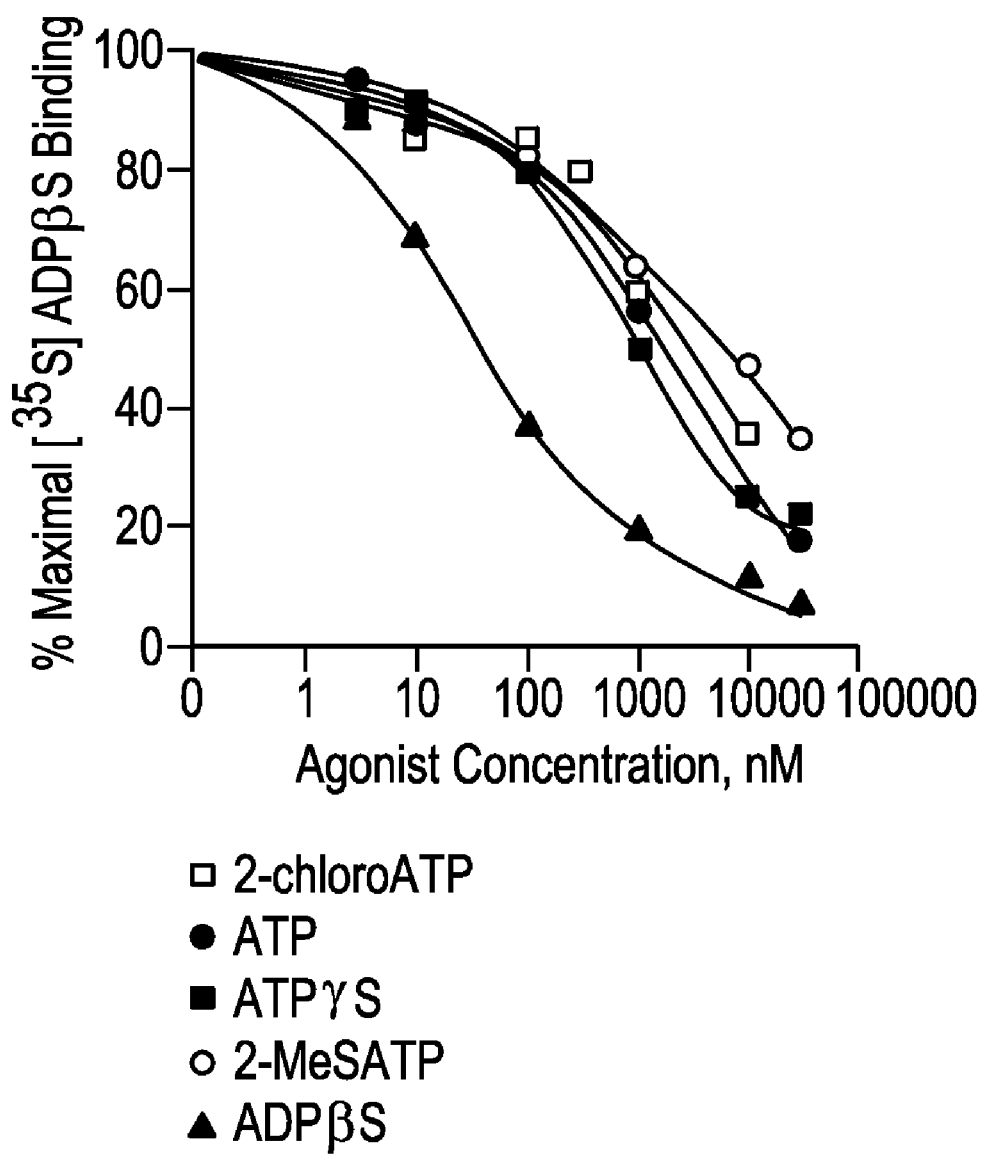

Part I: A series of compounds was tested for the ability to stimulate an increase in myocyte contractility. The ability to produce a positive inotropic response was compared to the ability to inhibit the high-affinity binding sites for [$^{35}$S] ADPβS. FIG. 3 shows the $EC_{50}$ values determined for each agonist stimulating myocyte contractility compared to the $K_i$ of the same agonists in inhibiting high-affinity [$^{35}$S] ADPβS binding. It can be seen that in general, the five compounds tested exhibit a strong positive inotropic responses which closely correspond to their Ki values.

Figure 4B:
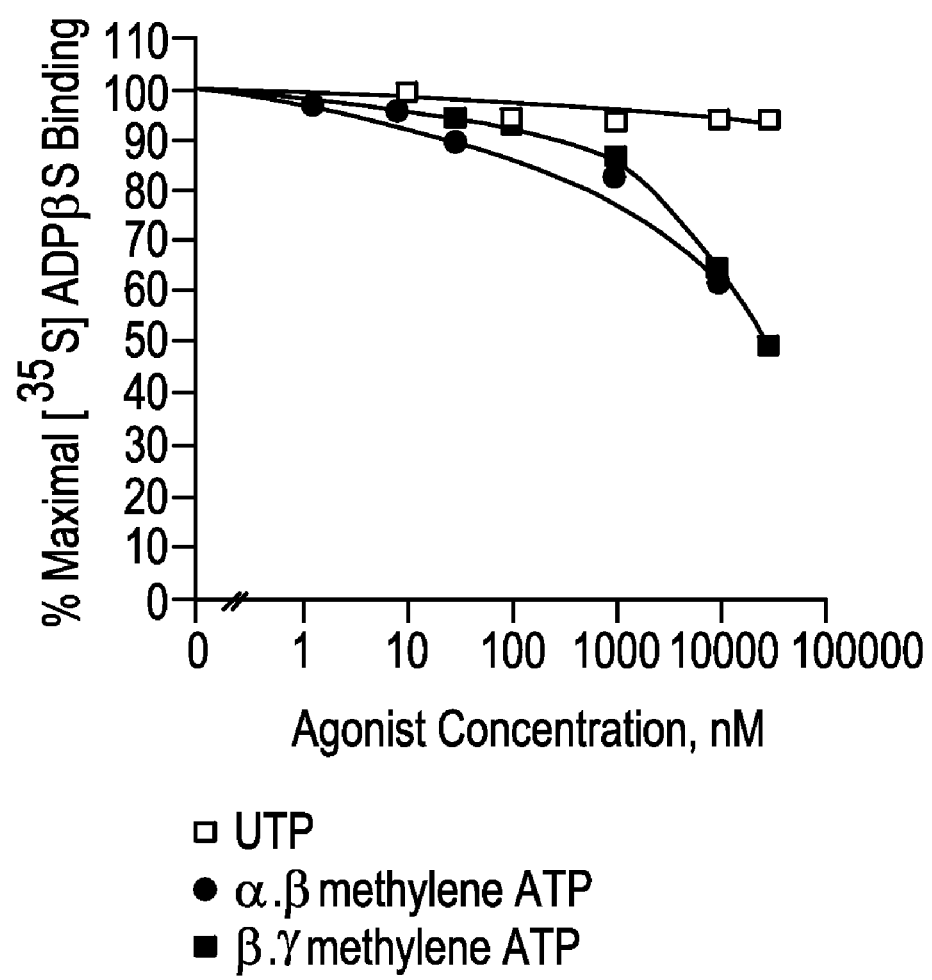

Part II: A second series of compounds were treated as in part I above. Although the $EC_{50}$ values for these compounds closely correspond to their Ki values, it can be seen from FIG. 4 that these compounds have a markedly diminished ability to stimulate myocyte contractility or to inhibit high-affinity [$^{35}$S] ADPβS binding.

EXAMPLE 4

Use of Cultured Chick Ventricular Cells and Adult Rat Cardiac Ventricular Cells as Models for the Characterization of Cardiac $P_2$ Purinergic Receptor Ventricular myocytes cultured from chick embryos 14 days in ovo and cells isolated from adult rat heart ventricles were used as novel cell models to characterize the cardiac P2PR. ATP caused a large increase in the contractile amplitude (maximal % increase=89.7±9%, n=14±SE), which was determined via a video motion detection system. ADP (47.7±10%, n=8), AMP (9.6±4%, n=7) and adenosine (15±4%, n=24) were much less efficacious. To determine the subtype of $P_2$PR involved, the ability of agonists selective at the $_{P2}$ (ADPβS and 2-methylthio ATP), $P2_x$ ($\alpha,\beta$-methylene ATP) and $P2_u$ (UTP) receptors to increase contractile amplitude were determined. The maximal percent increase was ADPβS>2-methylthio ATP (76±15%, n=7 and 54±7%, n=17, respectively)>>UTP (22±4%, n=7) or $\alpha,\beta$-methylene ATP (−13±5%, n=7). Prior exposure of the myocytes to 100 μM of 2-methylthio ATP for 60 minutes desensitized the positive inotropic response to ATP, ADPβS and UTP, whereas pretreatment of the myocytes with 100 μM UTP for three hours failed to cause such desensitization. These data validate the use of these cardiac cells as a model for the study of the cardiac receptor, and indicate that a $P_2$-like purinergic receptor mediates the positive inotropic response of ATP.

EXAMPLE 5

Figure 7A:
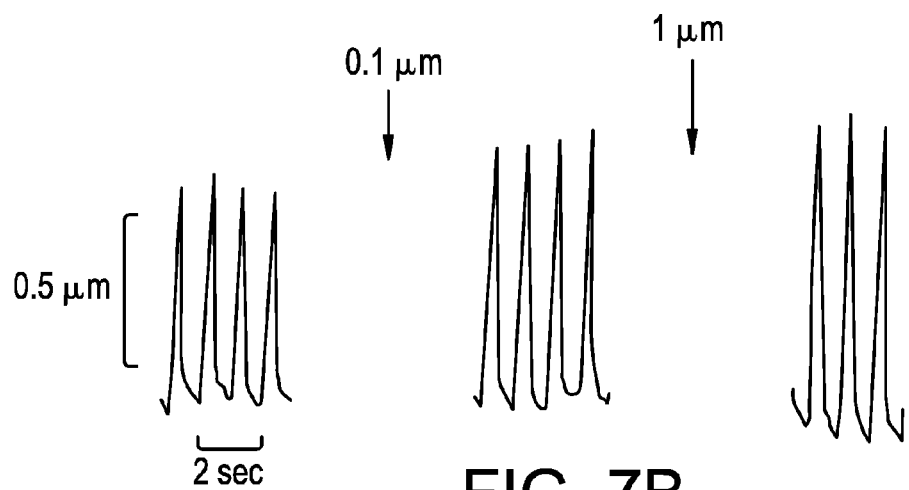
FIG. 7 shows the effects of adenosine 5'-monophosphoramidate, adenylyl 5'-phosphoramidate, and 2-methylthio ADP on the contractile amplitude of cardiac ventricular myocytes.
Figure 7B:
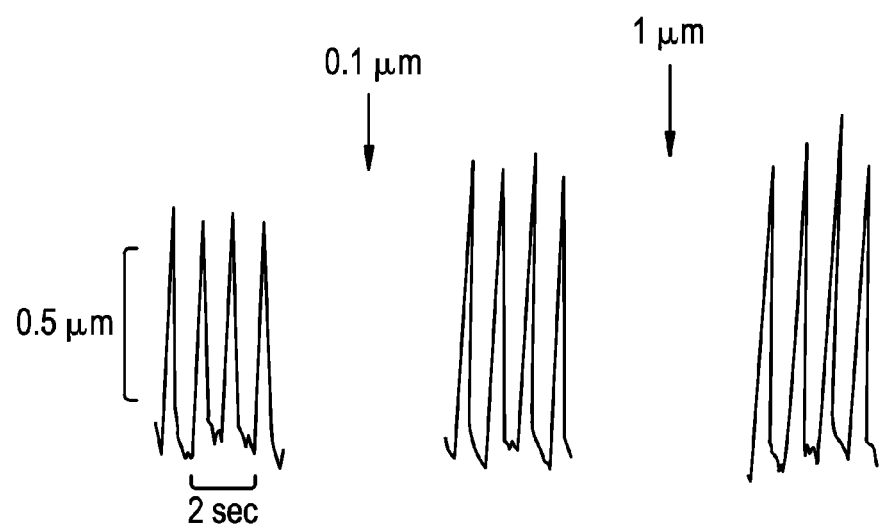
Figure 7C:
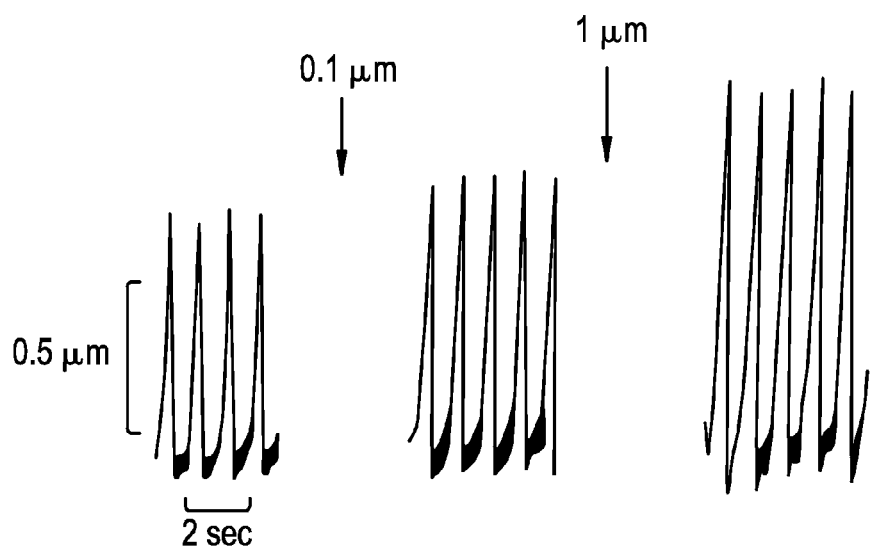

Effect of Nucleotides on the Cardiac Ventricular Myocytemyocyte Contractile Amplitude FIG. 7 shows the effect of nucleotides on cardiac ventricular myocytemyocyte contractile amplitude. Cardiac ventricular myocytes were prepared and the effects of (a) adenosine 5'monophosphoramidate, (b) adenylyl 5'phosphoramidate, and (c) 2-methylthio ADP on the basal contractile amplitude determined. The myocytes were paced at 2 HZ. The increase in contractile amplitude in response to various adenosine nucleotides was determined after a steady-state basal contraction was achieved. These data indicate that all three compounds have pronounced positive inotropic effect.

Figure 8A:
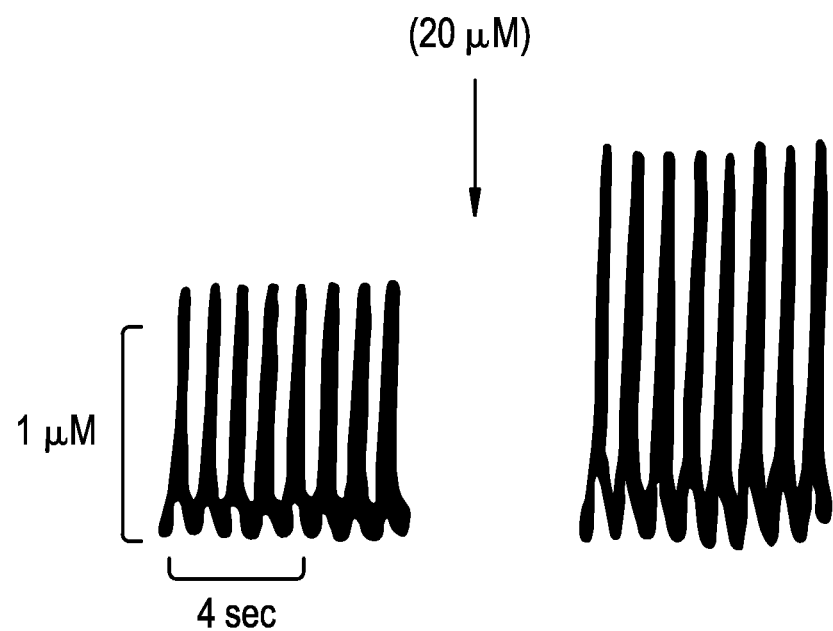
FIG. 8 shows the effects of adenylyl imidodiphospate and adenylyl imidodiphospate plus 8-sulfophenyltheophylline on the myocyte contractile amplitude.
Figure 8B:
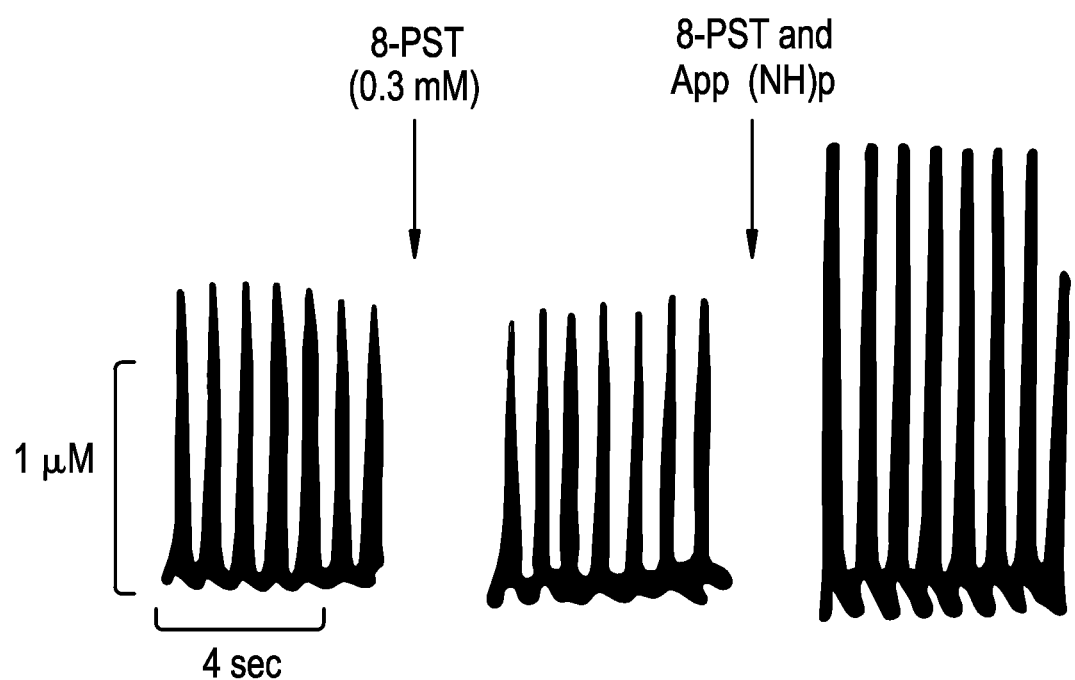

FIG. 8 shows the effect of a metabolically stable adenosine nucleotide on the myocyte contractile amplitude. Cardiac ventricular myocytes were prepared and the increase in basal contractile amplitude determined following exposure to the indicated concentrations of (a) adenylyl imidodiphospate (App(NH)p) or (b) App(NH)p plus 8-sulfophenyltheophylline (8-SPT). The compound 8-SPT is an adenosine receptor antagonist. These data indicate that App(NH)p has a pronounced positive inotropic effect which is not mediated via the adenosine receptor.

These data suggest that compounds with only one or two terminal phosphate groups have significant positive inotropic effect. The presence of an amide or a methyl group in the phosphate moiety of the nucleotides appears to render them more resistant to hydrolysis. Further, substitutions at the 2 position, particularly those with long-chain derivatives (see Fischer, B. et al., *J. Med. Chem.* 36: 3937-3946, 1993) will cause steric hindrance at the ectonucleotidase binding site, and thus minimize hydrolysis of the phosphate groups. The compounds of the present invention present a new generation of positive inotropes that are more stable, and that will find use as orally active agents in the treatment of disease states including congestive heart failure or any cause of cardiac dysfunction.

EXAMPLE 6

Synthesis of Compounds

A. Synthesis of compounds with 3'-modified ribose modifications

Figure 5:
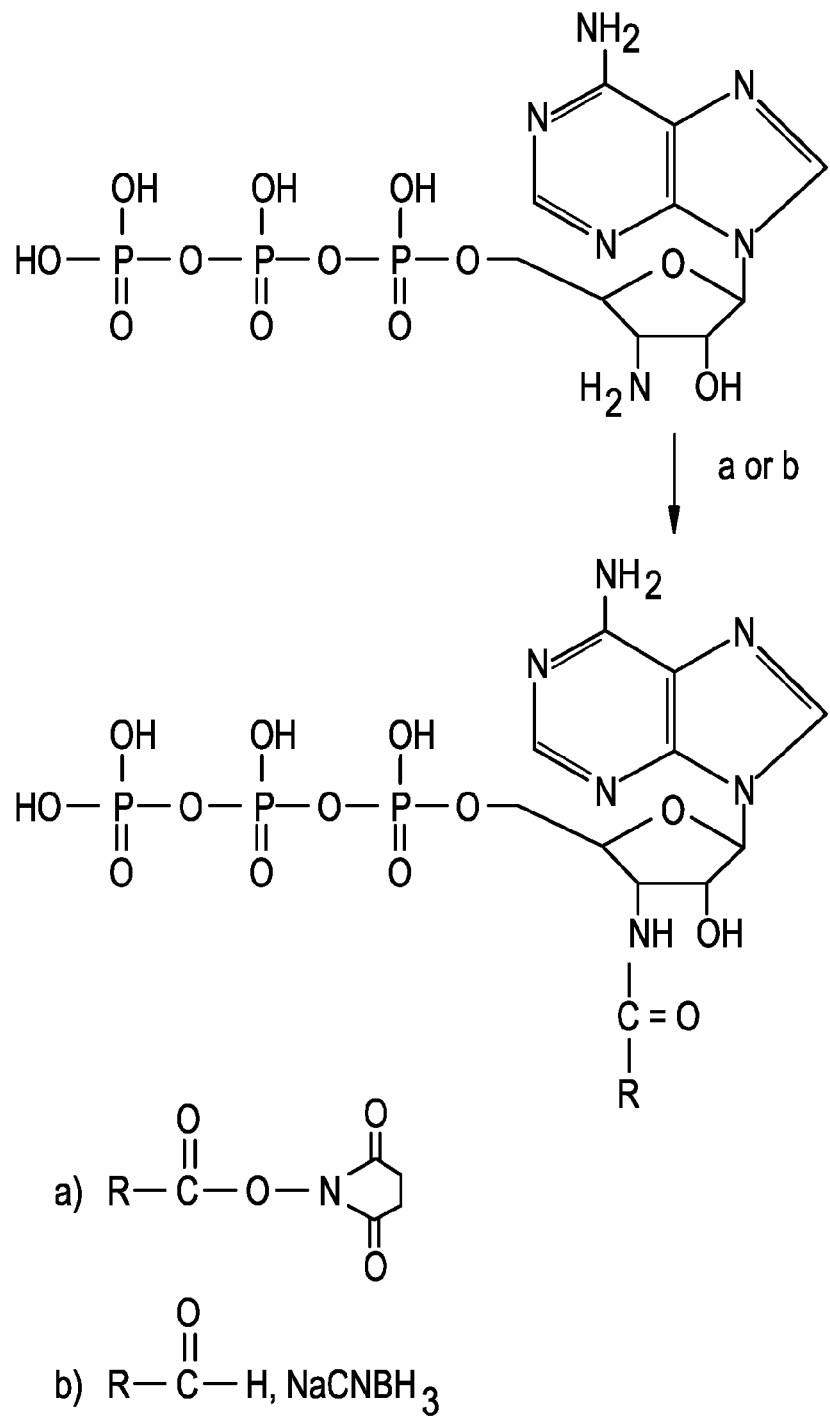
FIG. 5 shows the preparation of derivatives of 3'-amino-3' deoxy-ATP.

3'-Amino-3'-deoxyadenosine 5'-triphosphate and potassium carbonate are dissolved in water. 3-(4-Hydroxyphenyl) ethylene N-hydroxysuccinimide ester, 3-(4-hydroxy)phenylic N-hydroxysuccinimide ester, or 3-(4-hydroxyphenyl) pentylene N-hydroxysuccinimide ester in dimethylsulfoxide is added and the mixture is stirred at room temperature for 24 hours. The product is purified by repeated injection on HPLC using a Synchropak RP-100 column applying a linear gradient of acetonitrile 5-22% TEAA. The fractions are collected and lyophilized to dryness. The product is obtained as a triethylammonium salt. Derivatives of 3'-amino-3' deoxy-ATP are prepared by acylation of the amino group or its reductive alkylation with alkyl/aryl aldehyde and cyanoborohydride, as indicated in FIG. 5. See Burnstock, G., et al., Drug Development Research 31:206-219, 1994.

Figure 6A:
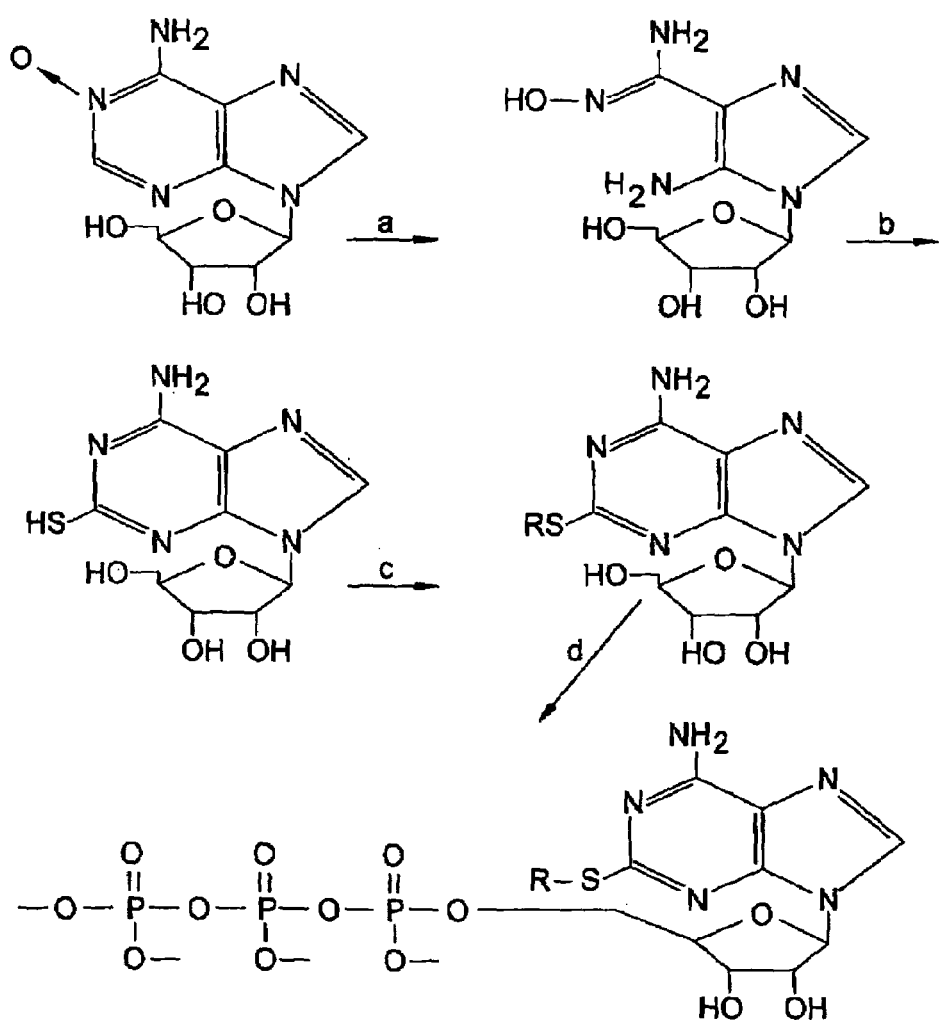
FIGS. 6a and 6b show the synthesis of 2-substituted ATP derivatives. (a=NaOH; b=$CS_2$; c=alkyl halide/NaOH or alkyl halide/triethylamine in DMF; d=$POCl_3$, tributylammonium pyrophosphate; R=—($CH_2$)CH=($CH_2$), —($CH_2$)$_x$—CN, p-($CH_2$)$_x$—$C_6H_4$—$NO_2$, —$CH_3$, —($CH_2$)$_x$—$CH_3$, —($CH_2$)$_x$—$C_6H_5$, cyclohexyl, cyclopentyl, phenyl, —($CH_2$)$_x$—C(O)OCH$_2$CH$_3$, where x is 1 to 7).
Figure 6B:
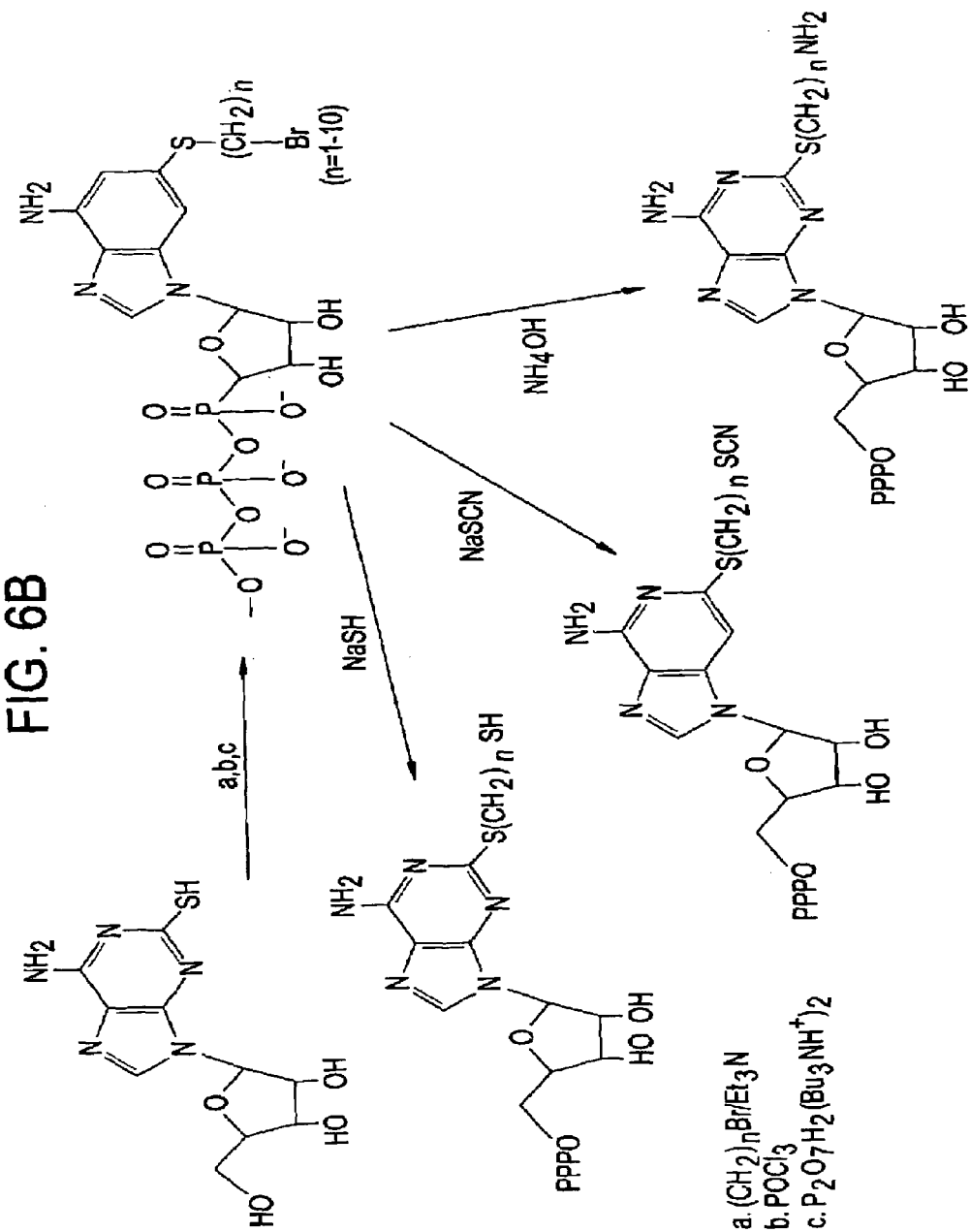

B. Synthesis of 2-substituted ATP Derivatives (FIGS. 6a and 6b)

The starting material, adenosine N-oxide, is prepared generally according to the procedure of Kikugawa, K., et al., A. Chem. Pharm. Bull. 25:1959, 1979. Adenosine N-oxide is added to a solution of 5 M NaOH, refluxed on an oil bath for 15 minutes and then rapidly chilled in ice-water and in dry-ice acetone. The pH is adjusted to 9 and the solution is evaporated on a rotary evaporator. The residue is taken up in methanol, and precipitated NaCl is removed by pressure filtration through fritted glass, which is washed with methanol and then evaporated. The product is then dissolved in water. The aqueous solution is mixed with methanol and carbon disulfide and heated in a pressure and heat-resistant vessel. The resulting 2-thioadenosine is then reacted with NaOH and then with ten equivalents of alkyl-aryl halide in the presence of ethanol. The reactions are evaluated by TLC (silica, CHC13/methanol 85:15 or CHC13/methanol/acetic acid 85:10:5). Once complete the product is crystallized by evaporation. At this point, the various 2-alkyl or aryl thioadenosine derivatives will be phosphorylated to the corresponding nucleoside mono-, di-, or tri-phosphates according to the method of Kovacs, T., et al., *Tetrahedron Letters*, 29(36): 4525-4528, 1988. The various nucleoside phosphates are isolated by HPLC using a gradient from O to 15% acetonitrile in 50 mM ammonium formate. The 2-alkyl/arylthioadenosine tri-phosphates will have a retention time ranging from 7 to 14 minutes.

Several $N^6$-substituted adenosine and 2-substituted derivatives which include a phenyl group, such as $N^6$-benzyladenosine, $N^6$-phenyladenosine, and 2-phenylaminoadenosine, are commercially available can be phosphorylated to the corresponding nucleoside mono-, di-, and triphosphates by the procedure of Kovacs, T., et al., supra.

C. Synthesis of 2,6-disubstituted ATP Derivatives

The third class of compounds include substitution at both the $N^6$ position and the 2-position. The starting compounds are the $N^6$-substituted derivatives, for example $N^6$-benzyladenosine, $N^6$-phenyladenosine or 2-phenylaminoadenosine, or $N^6$-methyladenosine which is also commercially available. These are first N-oxidized using m-chloroperbenzoic acid in acetic acid, and the $N^6$-substituted adenosine N-oxide is then substituted at the 2-position by a thio group, followed by alkylation with alkyl halide in NaOH to produce a 2-alkyl/aryl-thioadenosine derivative with substitution at the $N^6$ position. Such adenosine derivatives are phosphorylated to yield the corresponding nucleoside mono-, di-, and tri-phosphates according to the method of Kovacs, T., et al., supra. Groups suitable for 2-alkyl or aryl-thioadenosine substitution include all those outlined in FIGS. 6a and 6b.

D. Synthesis of ATP Derivatives Having Imidodiphosphate Functionality

ATP derivatives of formula IV having imidodiphosphate functionality are prepared in accordance with Scheme 1 below:

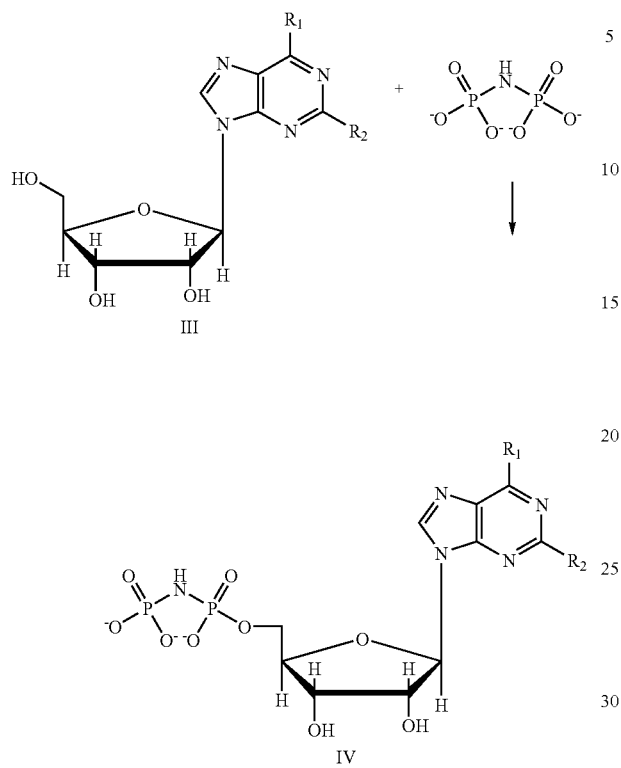

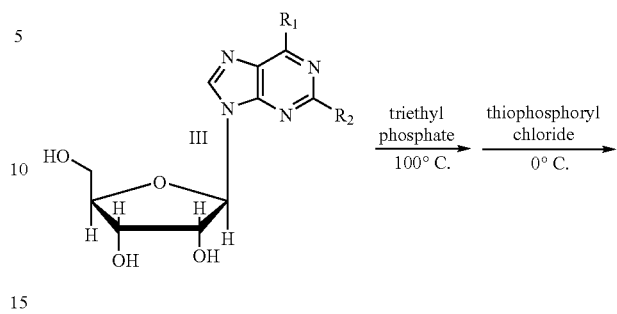

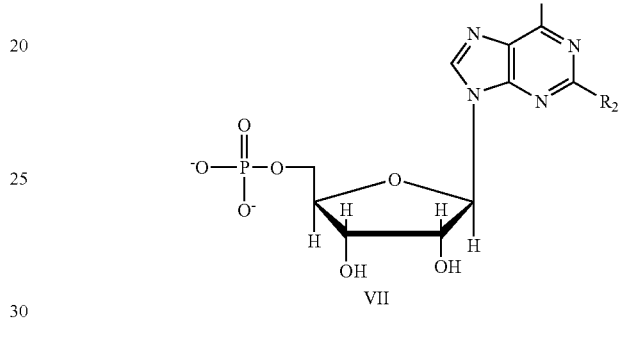

The nucleoside starting material of general formula III is prepared as described above and as shown in FIG. 6A. Tributylammonium imidodiphosphate, prepared from diphenylimidodiphosphoric acid according to the procedure of Nielsen et al., *J. Amer. Chem. Soc.* 83, 99-102 (1961), is then condensed with the compound of formula III according to the procedure of Yount et al., *Biochemistry* 10 (13) 2484-2489 (1971) to produce an ATP derivative of general formula IV having imidodiphosphate functionality. Purification is achieved by the procedure of Moffat, J., *Can. J. Biochem.*, 42, 599 (1961), as further described by Yount et al.

Figure 9:
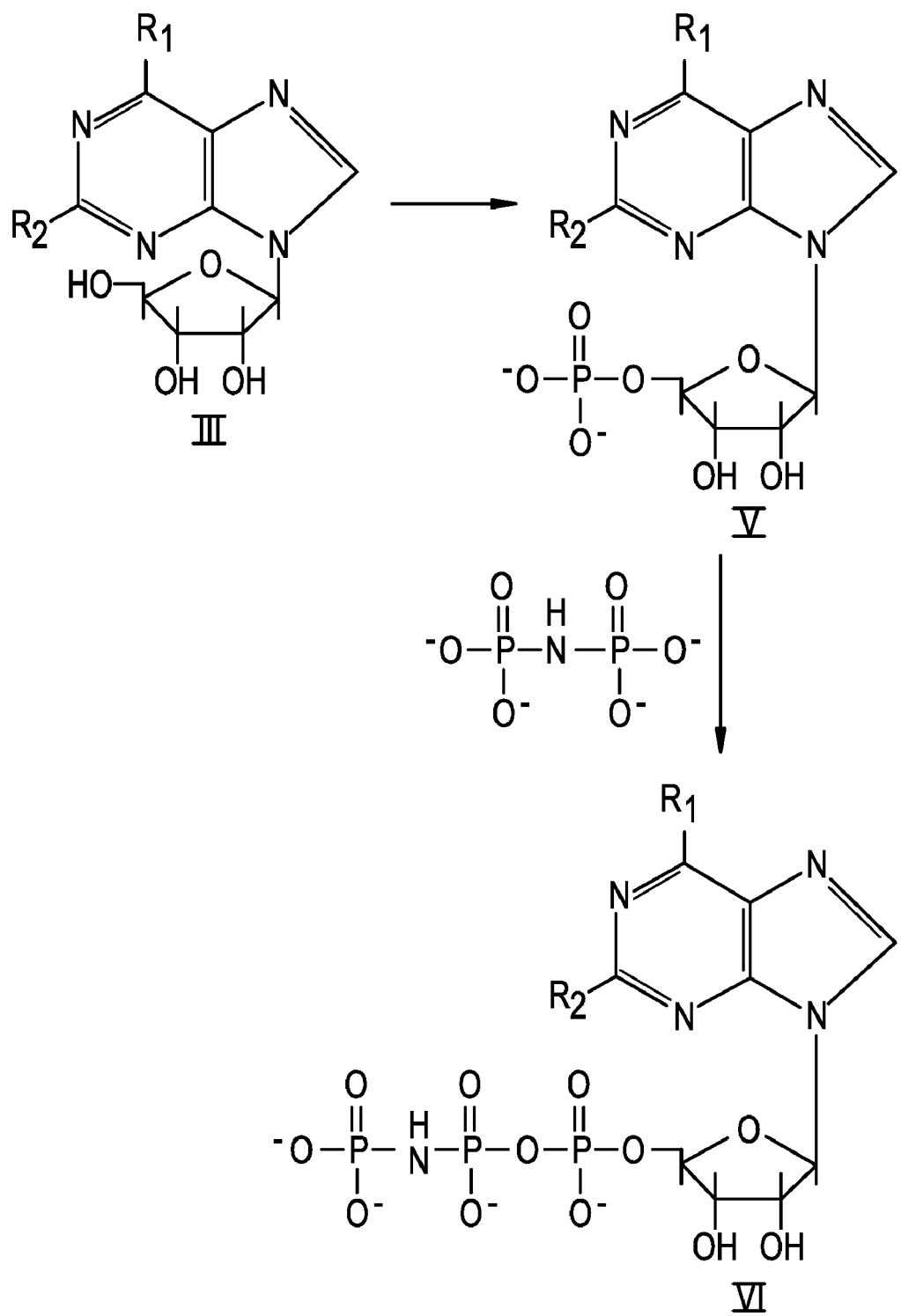
FIG. 9 shows the synthesis of imidodiphosphate-containing compounds of formula VI.

Imidodiphosphate-containing compounds of formula VI are prepared in accordance with FIG. 9. A compound of formula III is condensed with phosphoryl chloride in the presence of triethyl phosphate, followed by elution of the product from a column of Dowex AG 50 H$^+$ according to the procedure of MacFarlane et al., *J. Clin. Invest.* 71, 420-428 (1983). The isolated monophosphate of formula V is then condensed with tributylammonium imidodiphosphate, according to the procedure of Yount et al., supra, to produce the ATP derivative of formula VI.

E. Synthesis of Phosphorothioate Derivatives

Phosphorothioate derivatives are prepared from compounds of formula III by reaction with triethyl phosphate at 100° C. followed by thiophosphoryl chloride according to the procedure of Murray, A. W. and Atkinson, M. R., *Biochemistry* 7(11) 4023-4029 (1968), as summarized in Scheme 2 elow:

F. Synthesis of Monophosphate and Diphosphate Derivatives

5'-Monophosphate derivatives of formula V are prepared from compounds of formula III by reaction with phosphoryl chloride in the presence of triethyl phosphate as described above. 5'-Diphosphate derivatives are prepared from the derivatives of formula V by further reaction with N,N'-carbonyldiimidazole and tri-n-butylammonium phosphate according to MacFralane et al., supra.

G. Synthesis of Phosphonamide Derivatives

Compounds of formula VIII are prepared from compounds of formula V by reaction with the tributylammonium salt of disodium phosphoramidate according to the procedure of Yount et al., supra., as summarized in Scheme 3 below:

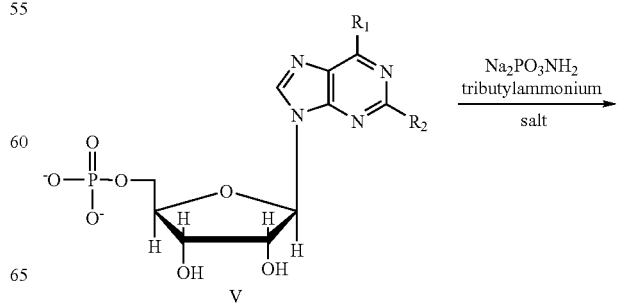

-continued

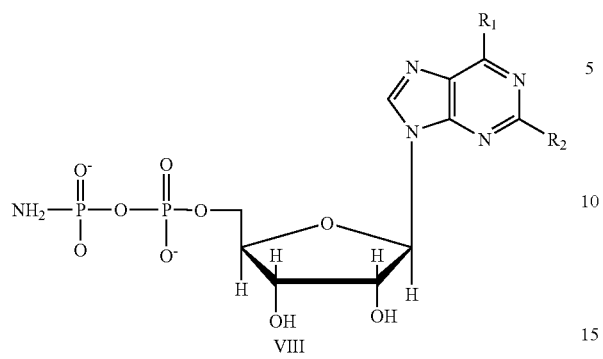

VIII

Compounds of formula IX are similarly prepared from compounds of formula III, as summarized by Scheme 4 below:

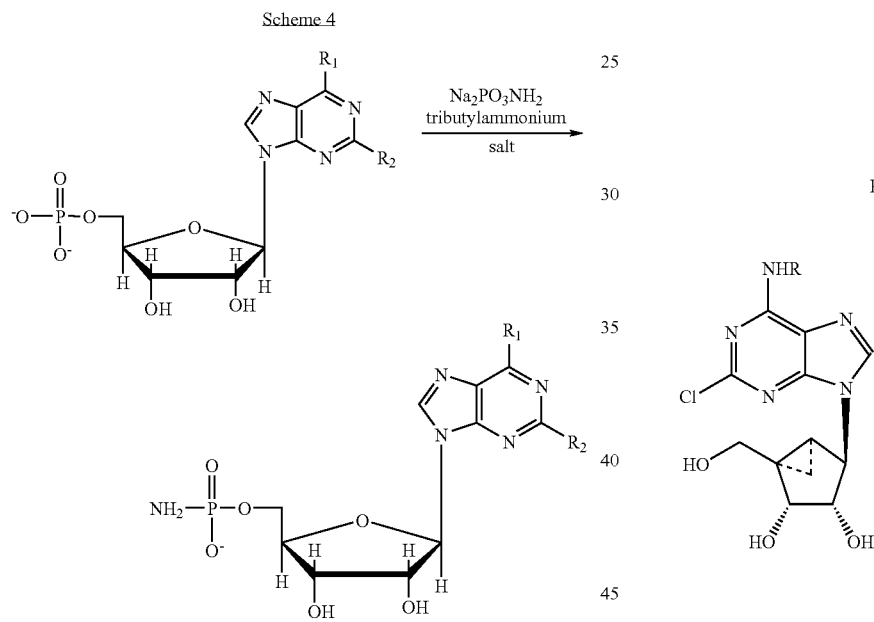

H. Synthesis of 2-hexyl AMP and 2-ethynyl AMP Compounds 2-hexyl AMP and 2-ethynl AMP are prepared according to the general procedures described by Abiru T. et al, *J. Med. Chem.* 2000, 35:2253-2260.

I. Synthesis of ATP Derivatives Having Methylene Functionality

α,β-methylene and β,γ-methylene ATP derivatives are prepared generally from 2-substituted adenosine derivatives, prepared as described above, according to the procedures of Cusack et al., *Biochem. J.* 1983 214:975-981.

J. Synthesis of 2-chlorosubstituted Methanocarbocyclic Analogues

Synthesis of 2-chlorosubstituted methanocarbocyclic analogues is accomplished according to the general methods of Jacobsen, et al. *J. Med. Chem.* 2000, 43, 2196-2203, which is shown below in Scheme 5.

Scheme 5

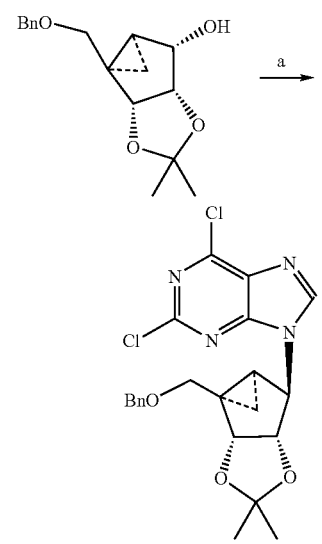

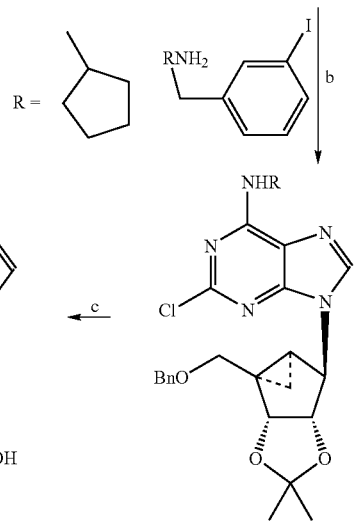

Reagents: (a) DEAD, Ph$_3$P; (b) MeOH, rt; (c) BCl$_3$

EXAMPLE 7

FIG. 10 demonstrates the increases in +dP/dt (cardiac muscle contractility) and −dP/dt (diastolic relaxation) that result in an isolated mouse heart when P2 agonists are present. Antegrade perfusion in the isolated heart was carried out using the work-performing model described as follows:

For the working heart model, a column of KHS buffer produced a constant hydrostatic pressure of 65 mmHg (for rat) or 55 mmHg (for mice). The opening of the pulmonary vein was connected via a PE-90 (for rat) or PE-50 (for mice) catheter to a reservoir of KHS buffer that maintained a "venous return" flow into the left atrium of about 12 mL/min (rat) or 5 mL/min (mice) under the resting condition. The venous return was maintained by a constant level of hydrostatic pressure (7-8 mm Hg) yielding a steady rate of venous return. The entering KHS buffer was then switched from retrograde to antegrade perfusion and produced a work-performing heart preparation. The perfusate exited the left ventricle through the aorta cannula, which was connected to the aortic column of KHS buffer with a hydrostatic pressure of 55 mmHg (for mice) or 65 mmHg (for rat). Aortic flow was the amount of perfusate exiting the aortic cannula measured in millimeters per minute. Coronary flow, in millimeters per minute, was collected via opening of the pulmonary artery. The sum of aortic flow and coronary flow was the cardiac output. A 23 gauge catheter was inserted into the left ventricle and its distal end is connected to a pressure transducer to record left ventricular pressures and ±dP/dt. The left ventricular developed pressure (LVDP) was the difference between LV systolic and diastolic pressure. A side port of the reservoir allowed direct infusion of beta-adrenergic agonist isoproterenol or P2X receptor agonist 2-meSATP into the KHS buffer that entered the left ventricle via the left atrium, which then entered the coronary circulation following ejection of drug-containing perfusate into the aorta.

The pressure recordings were channeled from amplifiers which had been precalibrated by a transducer simulator/calibrator (Ken Scientific Corp., Litchfield, Conn.). The signals were then digitized via a PCM-DAS 16S/330 interface board (Computer Boards, Inc. Mansfield, Mass.) which provided a high level of performance with analog input channels and digital channels. Data were analyzed by computer software (WorkBench for Windows+, Kent Scientific Corp.) designed for an IBM-compatible computer (Dell). The amplified and digitized signals from the transducers were constantly displayed and analyzed. Data acquisition, signal display (LV pressures, ±dP/dt, heart rate), and data analysis programs were run concurrently from the hard drive of the computer. Data points under each basal condition and during infusion of each drug concentration were summarized as means±SE, and the statistical differences were analyzed by one-way ANOVA with post-test comparison and t test.

2-meSATP and ISO (isoproterenol) were present at 100 nM. Basal represented the baseline values obtained before infusion with the agonists. Date were the means and standard errors of those obtained in 5 rats. The increases in +dP/dt, −dP/dt, and cardiac output (C.O.) by both agonists were statistically significant (P less than 0.05, paired t test). While 2-meSATP did not change the heart rate (H.R.), isoproterenol caused a significant stimulation of the H.R. (P less than 0.05, paired t test).

2-meSATP and isoproterenol were obtained from Sigma Chemical Co., St. Louis, Mo. Three month old CD-1 mice were obtained from Charles River (Cambridge, Mass.).

EXAMPLE 9

FIG. 11 demonstrates that 2-meSATP increases +dP/dt (an index of muscle contractility) and −dP/dt (an index of diastolic relaxation) in an intact working rat heart.

Those skilled in the art will appreciate that numerous changes and modifications may be made to the preferred embodiments of the invention and that such changes and modifications may be made without departing from the spirit of the invention. It is therefore intended that the appended claims cover all such equivalent variations as fall within the true spirit and scope of the invention.

What is claimed:

1. A method comprising the steps of
identifying an animal in need of treatment for heart failure; and
administering to said animal a compound of the following formula or a pharmaceutically acceptable salt thereof in an amount effective to treat said heart failure:

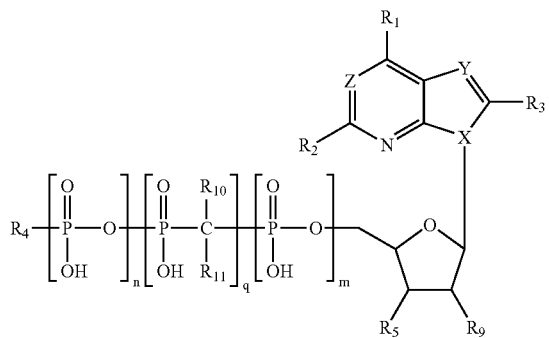

wherein
$R_1$ is halogen or $-R_6-(R_7)_p-R_8$;
$R_2$ is hydrogen, alkyl, cycloalkyl, cycloalkenyl, alkynyl, alkylthio, aminoalkylthio, halogen, or $-R_6-(R_7)_p-R_8$;
$R_3$ is H, halogen or $-R_6-(R_7)_p-R_8$;
$R_4$ is —OH or —SH;
$R_5$ is —OH or acetamido;
$R_6$ is NH or S;
$R_7$ is $CH_2$;
$R_8$ is H, $NH_2$, halogen, CN, CCH, cycloalkyl, having 3 to about 10 carbon atoms or aryl having 3 to about 20 carbon atoms;
$R_9$ is OH;
$R_{10}$ and $R_{11}$ are independently hydrogen or halogen;
X, Y, and Z are;
m is 0, 1, or 2;
n is 0 or 1;
q is 0 or 1 with the proviso that when q is 0, then $R_2$ is alkyl, cycloalkyl, cycloalkenyl, alkynyl, halogen, or $-R_6-(R_7)_p-R_8$ where $R_6$ is NH, provided that at least one of m, n, and q is 1; and
p is 0 to 10.

2. The method of claim 1 wherein $R_2$ is halogen or alkylthio.

3. The method of claim 1 wherein $R_2$ is Cl.

4. A method comprising the steps of:
identifying an animal in need of treatment for heart failure; and
administering to said animal a compound of the following formula or a pharmaceutically acceptable salt thereof in an amount effective to treat said heart failure:

25

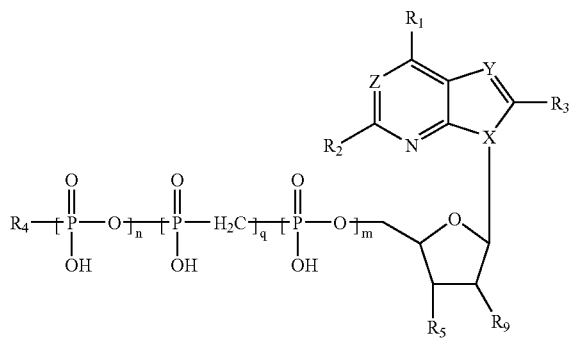

wherein
 $R_1$ is halogen or —$R_6$—($R_7$)$_p$—$R_8$;
 $R_2$ is hydrogen, alkyl, cycloalkyl, cycloalkenyl, alkynyl, alkiylthio, aininoalkylthio, halogen, or —$R_6$—($R_7$)$_p$—$R_8$
 $R_3$ is H, halogen or —$R_6$—($R_7$)$_p$—$R_8$;
 $R_4$ is —OH or —SH;
 $R_5$ is —OH or acetamido;
 $R_6$ is NH or S
 $R_7$ is $CH_2$
 $R_8$ is H, $NH_2$, halogen, CN, CCH, cycloalkyl, having 3 to about 10 carbon atoms or aryl having 3 to about 20 carbon atoms;
 $R_9$ is OH;
 X, Y, and Z are N;
 m is 0, 1, or 2;
 n is 0 or 1;
 q is 0 or 1 with the proviso that when q is 0, then $R_2$ is alkyl, cycloalkyl, cycloalkenyl, alkynyl, halogen, or —$R_6$—($R_7$)$_p$—$R_8$ where $R_6$ is NH; and
 p is 0 to 10.

5. The method of claim 4 wherein $R_2$ is alkyl.
6. The method claim 5 wherein $R_1$ is $NH_2$.
7. The method of claim 6 wherein $R_4$ is —OH.
8. The method of claim 6 wherein the sum of m and n is 1 and q is 0.
9. The method of claim 5 wherein $R_2$ is $C_3$ to $C_{10}$ alkyl.
10. The method of claim 9 wherein $R_2$ is $C_6$ alkyl.
11. The method of claim 4 wherein $R_2$ is —C≡CH.
12. The method of claim 4 wherein $R_3$ is H and q is 1.
13. The method of claim 12 wherein $R_2$ is —S-alkyl.
14. The method of claim 13 wherein $R_2$ is —S—$C_6H_{13}$.
15. The method of claim 4 wherein $R_5$ is acetamido.
16. The method of claim 15 wherein $R_2$ is halogen.
17. The method of claim 15 wherein $R_2$ is Cl.
18. The method of claim 17 wherein q is 0 and the sum of m and n is 3.
19. The method of claim 4 wherein $R_2$ is alkylthio.
20. The method of claim 19 wherein the sum of m and n is 2 and q is 0.
21. The method of claim 4 wherein $R_2$ is $R_6$—($R_7$)$_p$—$R_8$.
22. The method of claim 21 wherein $R_2$ is-4-aminophenylethylthio.
23. The method of claim 4 wherein said animal is a mammal.
24. The method of claim 4 wherein said heart failure is due to myocardial infarction, rheumatic heart disease, infection of the myocardium, and viral infection of the heart.

26

25. A method comprising the steps of:
 identifying cardiac muscle tissue in need of increased cardiac muscle contractility; and
 contacting said cardiac muscle tissue with a compound having the formula:

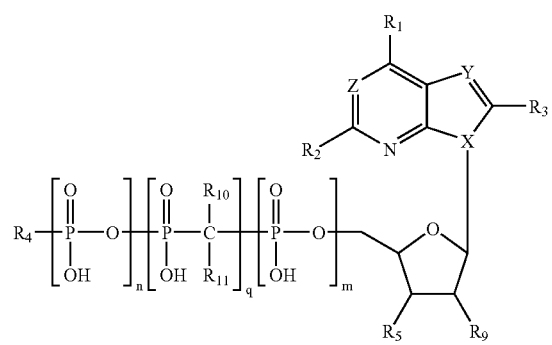

wherein
 $R_1$ is halogen or —$R_6$—($R_7$)$_p$—$R_8$;
 $R_2$ is hydrogen, alkyl, cycloalkyl, cycloalkenyl, alkynyl, alkylthio, aminoalkylthio, halogen, or —$R_6$—($R_7$)$_p$—$R_8$;
 $R_3$ is H, halogen or —$R_6$—($R_7$)$_p$—$R_8$;
 $R_4$ is —OH or —SH;
 $R_5$ is —OH or acetamido;
 $R_6$ is NH or S;
 $R_7$ is $CH_2$;
 $R_8$ is H, $NH_2$, halogen, CN, CCH, cycloalkyl, having 3 to about 10 carbon atoms or aryl having 3 to about 20 carbon atoms;
 $R_9$ is OH;
 $R_{10}$ and $R_{11}$ are independently hydrogen or halogen;
 X, Y, and Z are N;
 m is 0, 1, or 2;
 n is 0 or 1;
 q is 0 or 1 with the proviso that when q is 0, then $R_2$ is alkyl, cycloalkyl, cycloalkenyl, alkynyl, halogen, or —$R_6$—($R_7$)$_p$—$R_8$ where R6 is NH;
 provided that at least one of q, n, and m is 1; and
 p is 0 to 10.

26. The method of claim 25 wherein $R_2$ is Cl.
27. A method comprising the steps of:
 identifying cardiac muscle tissue in need of increased cardiac muscle contractility; and
 contacting said cardiac muscle tissue with a compound having the formula:

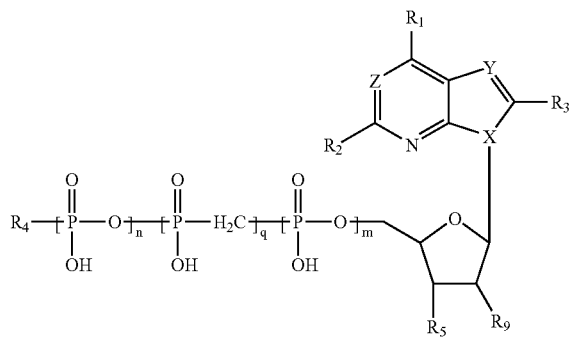

wherein
R$_1$ is halogen or —R$_6$—(R$_7$)$_p$—R$_8$;
R$_2$ is hydrogen, alkyl, cycloalkyl, cycloalkenyl, alkynyl, alkylthio, aminoalkyl, halogen, or —R$_6$—(R$_7$)$_p$R$_8$;
R$_3$ is H, halogen or —R$_6$—(R$_7$)$_p$—R$_8$;
R$_4$ is —OH or —SH;
R$_5$ is —OH or acetamido;
R$_6$ is NH or S;
R$_7$ is CH$_2$;
R$_8$ is H, NH$_2$, halogen, CN, CCH, cycloalkyl, having 3 to about 10 carbon atoms or aryl having 3 to about 20 carbon atoms;
R$_9$ is OH;
X, Y, and Z are N;
m is 0, 1, or 2;
n is 0 or 1;
q is 0 or 1 with the proviso that when q is 0, then R$_2$ is alkyl, cycloalkyl, cycloalkenyl, alkynyl, halogen, or —R$_6$—(R$_7$)$_p$—R$_8$ where R$_6$ is NH, provided that at least one of q, n, and m is 1; and
p is 0 to 10.

28. The method of claim 27 wherein R$_3$ is H.

29. The method of claim 28 wherein the sum of m and n is 1 and q is 0.

30. The method of claim 29 wherein R$_2$ is alkyl, cycloalkyl, or alkynyl.

31. The method of claim 30 wherein R$_2$ is hexyl or —C≡CH.

32. The method of claim 27 further comprising measuring a rate of contraction associated with said cardiac muscle tissue.

33. The method of claim 27 wherein the sum of n and m is 2 and q is 0.

34. The method of claim 27 wherein the sum of m, n, and q is 3 and q is 0 or 1.

35. The method of claim 34 wherein R$_2$ is alkylthio, H, or Cl.

36. A method comprising the steps of: identifying cardiac muscle tissue in need of diastolic cardiac relaxation; and contacting said cardiac muscle tissue with a compound having the formula:

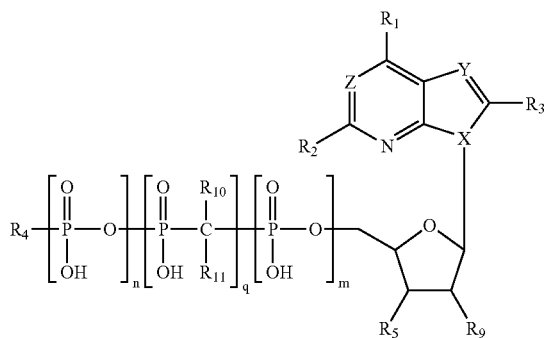

wherein
R$_1$ is halogen or —R$_6$—(R$_7$)$_p$—R$_8$;
R$_2$ is hydrogen, alkyl, cycloalkyl, cycloalkenyl, alkynyl, alkylthio, aminoalkylthio, halogen, or —R$_6$—(R$_7$)$_p$—R$_8$;
R$_3$ is H, halogen or —R$_6$—(R$_7$)$_p$—R$_8$;
R$_4$ is —OH or —SH;
R$_5$ is —OH or acetamido;
R$_6$ is NH or S;
R$_7$ is CH$_2$;
R$_8$ is H, NH$_2$, halogen, CN, CCH, cycloalkyl, having 3 to about 10 carbon atoms or aryl having 3 to about 20 carbon atoms;
R$_9$ is OH;
R$_{10}$ and R$_{11}$ are independently hydrogen or halogen;
X, Y, and Z are N;
m is 0, 1, or 2;
n is 0 or 1;
q is 0 or 1 with the proviso that when q is 0, then R$_2$ is alkyl, cycloalkyl, cycloalkenyl, alkynyl, halogen, or —R$_6$—(R$_7$)$_p$—R$_8$ where R$_6$ is NH, provided that at least one of m, n, and q is 1; and
p is 0 to 10.

37. A method comprising the steps of:
identifying cardiac muscle tissue in need of diastolic cardiac relaxation; and
contacting said cardiac muscle tissue with a compound having the formula:

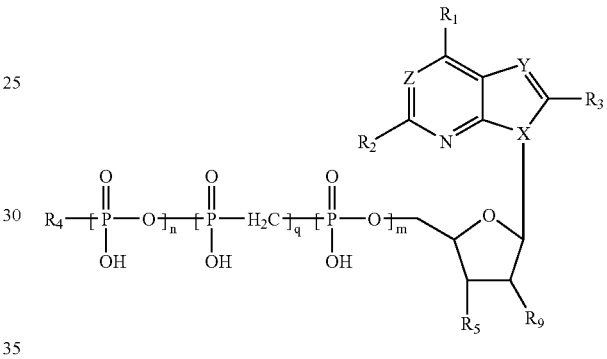

wherein
R$_1$ is halogen or —R$_6$—(R$_7$)$_p$—R$_8$;
R$_2$ is hydrogen, alkyl, cycloalkyl, cycloalkenyl, alkynyl, alkylthio, aminoalkyl, halogen, or —R$_6$—(R$_7$)$_p$—R$_8$;
R$_3$ is H, halogen or —R$_6$—(R$_7$)$_p$—R$_8$;
R$_4$ is —OH or —SH;
R$_5$ is —OH or acetamido;
R$_6$ is NH or S
R$_7$ is CH$_2$
R$_8$ is H, NH$_2$, halogen, CN, CCH, cycloalkyl, having 3 to about 10 carbon atoms or aryl having 3 to about 20 carbon atoms;
R$_9$ is OH;
X, Y, and Z are N;
m is 0, 1, or 2;
n is 0 or 1;
q is 0 or 1 with the proviso that when q is 0, then R$_2$ is alkyl, cycloalkyl, cycloalkenyl, alkynyl, halogen, or —R$_6$—(R$_7$)$_p$—R$_8$ where R$_6$ is NH, provided that at least one of m, n, and q is 1; and
p is 0 to 10.

38. The method of claim 37 wherein X, Y, and Z are N and the sum of m and n is 1 and q is 0.

39. The method of claim 37 wherein R$_2$ is hexylthio, heptylthio, undecylthio, hexyl, ethynyl, cyclohexyl, cyclohexyl, or a substituted phenylethylthio.

40. The method of claim 37 wherein the sum of m and n is 3 and q is 0.

41. The method of claim 40 wherein R$_2$ is H, halogen, hexylthio, or methylthio.

42. The method of claim 37 wherein q is 0 and the sum of n and m is 2.

43. The method of claim 42 wherein $R_2$ is alkylthio.

44. The method of claim 37 wherein the sum of m, n, and q is 3 and q is 1.

45. The method of claim 44 wherein $R_2$ is alkylthio.

46. A method comprising the steps of:
identifying an animal in need of vasodilation; and
administering to said animal an amount effective to cause said vasodilation of a compound having the following formula or a pharmaceutically acceptable salt thereof:
contacting said cardiac muscle tissue with a compound having the formula:

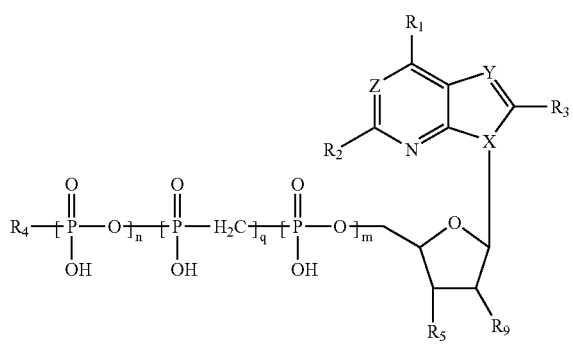

wherein
$R_1$ is halogen or $-R_6-(R_7)_p-R_8$;
$R_2$ is hydrogen, alkyl, cycloalkyl, cycloalkenyl, alkynyl, alkylthio, aminoalkyltbio, halogen, or $-R_6-(R_7)_p-R_8$;
$R_3$ is H, halogen or $-R_6-(R_7)_p-R_8$;
$R_4$ is $-$OH or $-$SH;
$R_5$ is $-$OH acetamido;
$R_6$ is NH or S;
$R_7$ is $CH_2$;
$R_8$ is H, $NH_2$, halogen, CN, CCH, cycloalkyl, having 3 to about 10 carbon atoms or aryl having 3 to about 20 carbon atoms;
$R_9$ is OH;
X, Y, and Z are N;
m is 0, 1, or 2;
n is 0 or 1;
q is 0 or 1 with the proviso that when q is 0, then $R_2$ is alkyl, cycloalkyl, cycloalkenyl, alkynyl, halogen, or $-R_6-(R_7)_p-R_8$ where $R_6$ is NH, provided that at least one of m, n, and q is 1; and
p is 0 to 1.

* * * * *